(12) United States Patent
Calisse

(10) Patent No.: US 11,324,862 B2
(45) Date of Patent: May 10, 2022

(54) ENDOLUMINAL DEVICE

(71) Applicant: B. BRAUN MELSUNGEN AG, Melsungen (DE)

(72) Inventor: Jorge Calisse, Berlin (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 77 days.

(21) Appl. No.: 16/478,668

(22) PCT Filed: Jan. 25, 2017

(86) PCT No.: PCT/EP2017/051531
§ 371 (c)(1),
(2) Date: Jul. 17, 2019

(87) PCT Pub. No.: WO2018/137763
PCT Pub. Date: Aug. 2, 2018

(65) Prior Publication Data
US 2020/0254150 A1    Aug. 13, 2020

(51) Int. Cl.
*A61F 2/86* (2013.01)
*A61F 2/88* (2006.01)
(Continued)

(52) U.S. Cl.
CPC ............... *A61L 31/06* (2013.01); *A61F 2/07* (2013.01); *A61F 2/86* (2013.01); *A61F 2/885* (2013.01);
(Continued)

(58) Field of Classification Search
CPC ...... A61F 2/06; A61F 2/07; A61F 2/82; A61F 2/86; A61F 2/885; A61F 2/90;
(Continued)

(56) References Cited

U.S. PATENT DOCUMENTS 5,843,158 A   12/1998 Lenker et al.
9,566,367 B2  2/2017 Stekker et al.
(Continued)

FOREIGN PATENT DOCUMENTS

CN   101496754 A   8/2009
CN   102307542 A   1/2012
(Continued)

OTHER PUBLICATIONS

International Search Report and Written Opinion for International Application No. PCT/EP2017/051531, dated Oct. 9, 2017—8 pages.
(Continued)

*Primary Examiner* — Dinah Baria
(74) *Attorney, Agent, or Firm* — Culhane Meadows PLLC; Christopher A. Rothe

(57) ABSTRACT

An endoluminal device includes a composite yarn with a polymer yarn and an alloy wire. The polymer yarn includes a biodegradable polymer, and the alloy wire includes a biocompatible alloy. An endoluminal device can include a plurality of polymer yarns and at least one alloy wire, in which the polymer yarns include a biodegradable polymer, and the least one alloy wire includes a biocompatible alloy. A surgical system or kit includes an endoluminal device and a delivery instrument.

19 Claims, 6 Drawing Sheets

Figure 1:
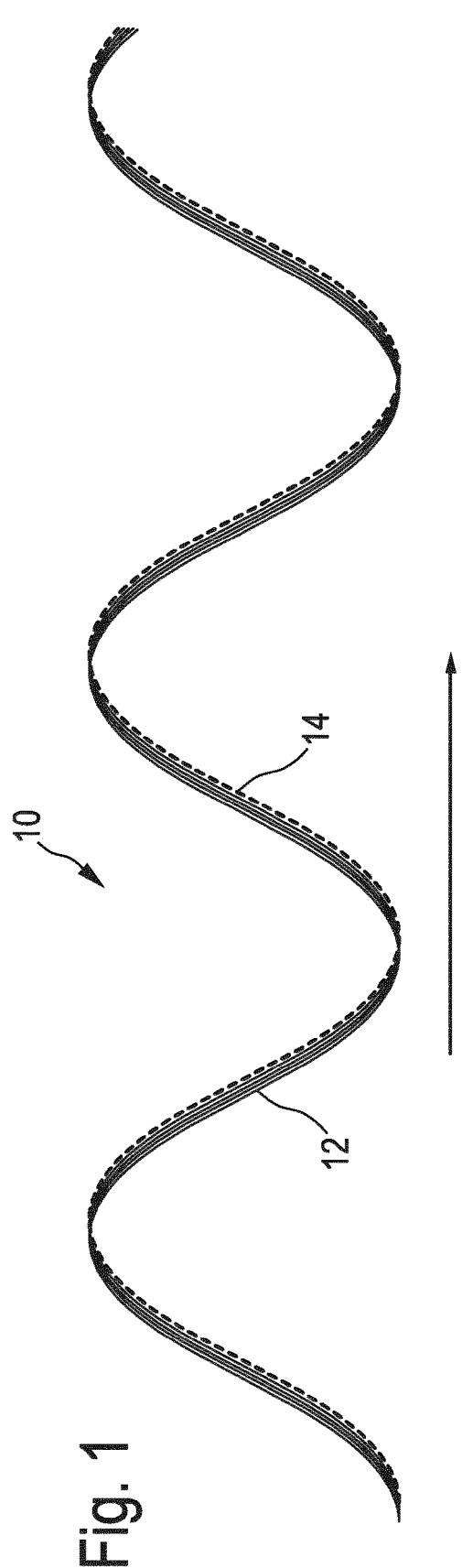

(51) Int. Cl.
*A61L 31/06* (2006.01)
*A61L 31/02* (2006.01)
*A61L 31/14* (2006.01)
*A61F 2/07* (2013.01)

(52) U.S. Cl.
CPC ........... *A61L 31/022* (2013.01); *A61L 31/148* (2013.01); *A61F 2210/0004* (2013.01); *A61F 2230/0091* (2013.01)

(58) Field of Classification Search
CPC .... A61F 2210/0004; A61F 2310/00041; A61F 2310/00011; A61L 31/022; A61L 31/148
See application file for complete search history.

(56) References Cited

U.S. PATENT DOCUMENTS

| | | |
|---|---|---|
| 10,004,834 B2 | 6/2018 | Hossainy et al. |
| 2006/0052864 A1 | 3/2006 | Harder et al. |
| 2010/0016940 A1 | 1/2010 | Shokoohi et al. |
| 2010/0082093 A1 | 4/2010 | Weber |
| 2011/0230955 A1* | 9/2011 | Orion ................ A61F 2/064 623/1.15 |
| 2011/0319977 A1 | 12/2011 | Pandelidis et al. |
| 2012/0158123 A1 | 6/2012 | Borck |
| 2013/0317590 A1 | 11/2013 | Huang et al. |
| 2015/0081000 A1 | 3/2015 | Hossainy et al. |
| 2020/0254150 A1 | 8/2020 | Calisse |

FOREIGN PATENT DOCUMENTS

| | | |
|---|---|---|
| CN | 102335052 A | 2/2012 |
| CN | 104720941 A | 6/2015 |
| CN | 105530895 A | 4/2016 |
| EP | 1632255 A2 | 3/2006 |
| EP | 2465551 A2 | 6/2012 |
| EP | 2559408 A2 | 2/2013 |
| EP | 2647394 A2 | 10/2013 |
| EP | 2647484 A1 | 10/2013 |
| EP | 3085339 A1 | 10/2016 |
| EP | 3120877 A1 | 1/2017 |
| JP | 2005514106 A | 5/2005 |
| JP | 2016116633 A | 6/2016 |
| JP | 3206584 U | 9/2016 |
| JP | 2018007802 A | 1/2018 |
| WO | 0074744 A1 | 12/2000 |
| WO | 2007126598 A2 | 11/2007 |
| WO | 2007139668 A2 | 12/2007 |
| WO | 2011117298 A1 | 9/2011 |
| WO | 2013024124 A1 | 2/2013 |
| WO | 2013052856 A2 | 4/2013 |

OTHER PUBLICATIONS

Office Action received in Japanese Application No. 2019-560458 dated Jan. 5, 2021, with translation, 6 pages.
Jianjun, et al., "Clinical Application of Drug-Eluting Stents," received in Application No. 201780088570.2, People's Military Medical Press Beijing, Nov. 30, 2006, with translation, 12 pages.
Office Action received Chinese Application No. 201780088570.2 dated Jun. 18, 2021, with translation, 29 pages.

* cited by examiner

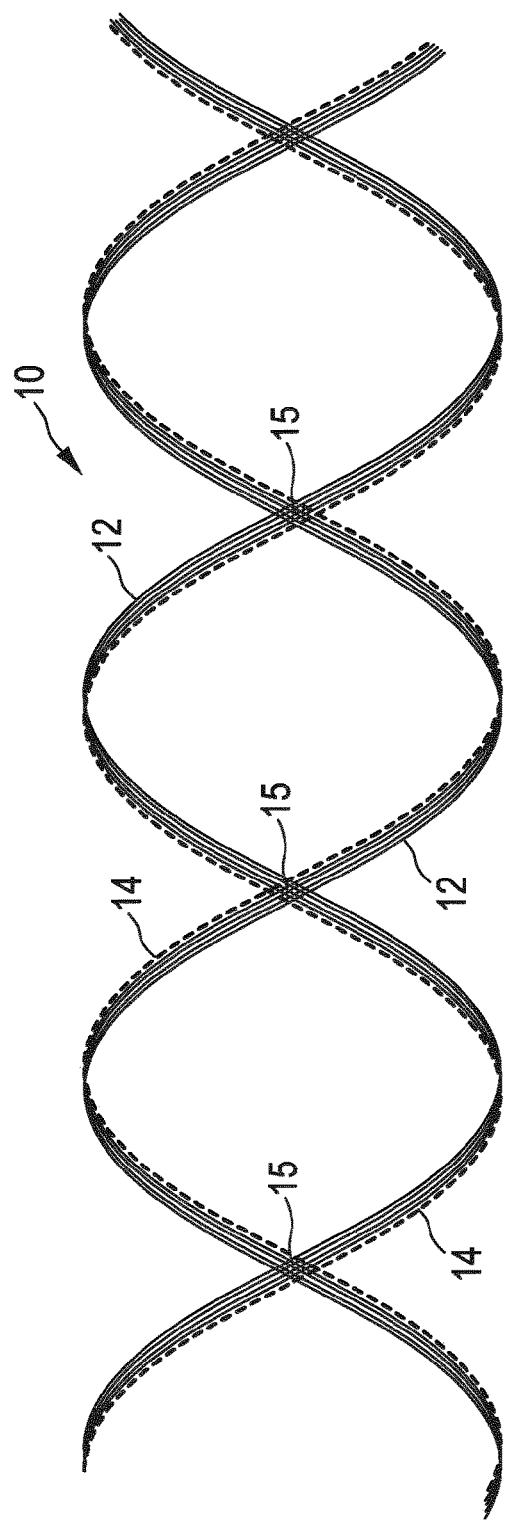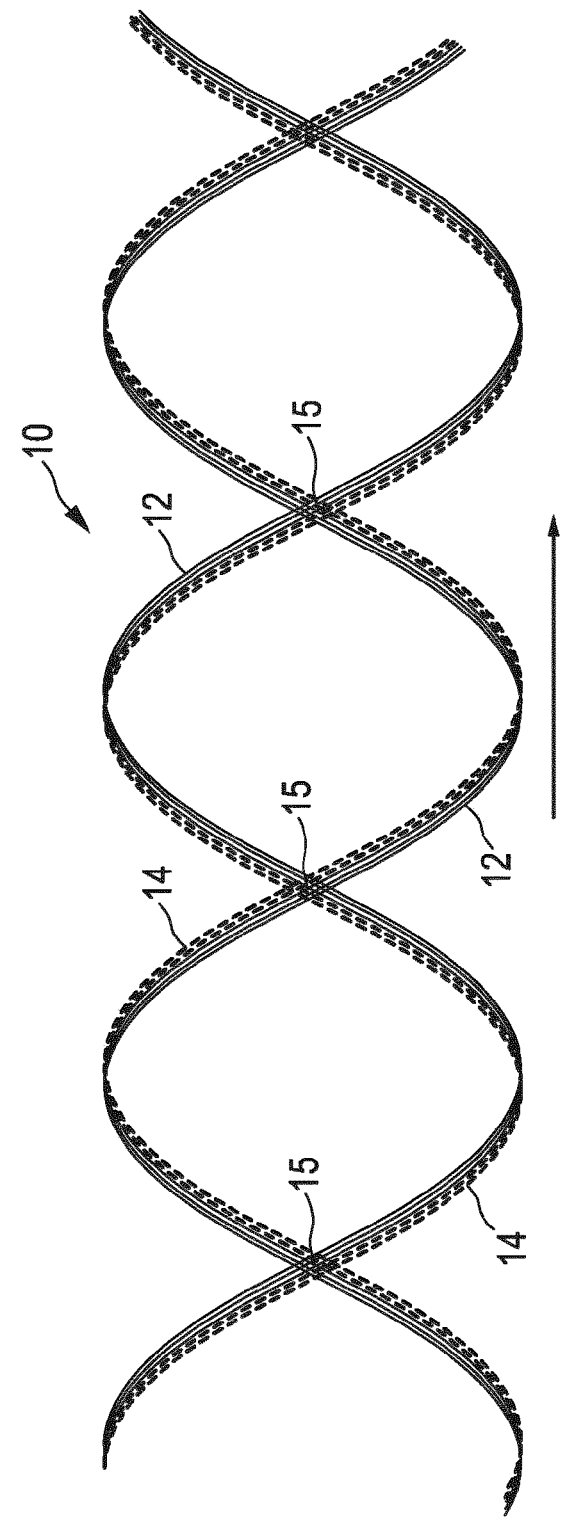

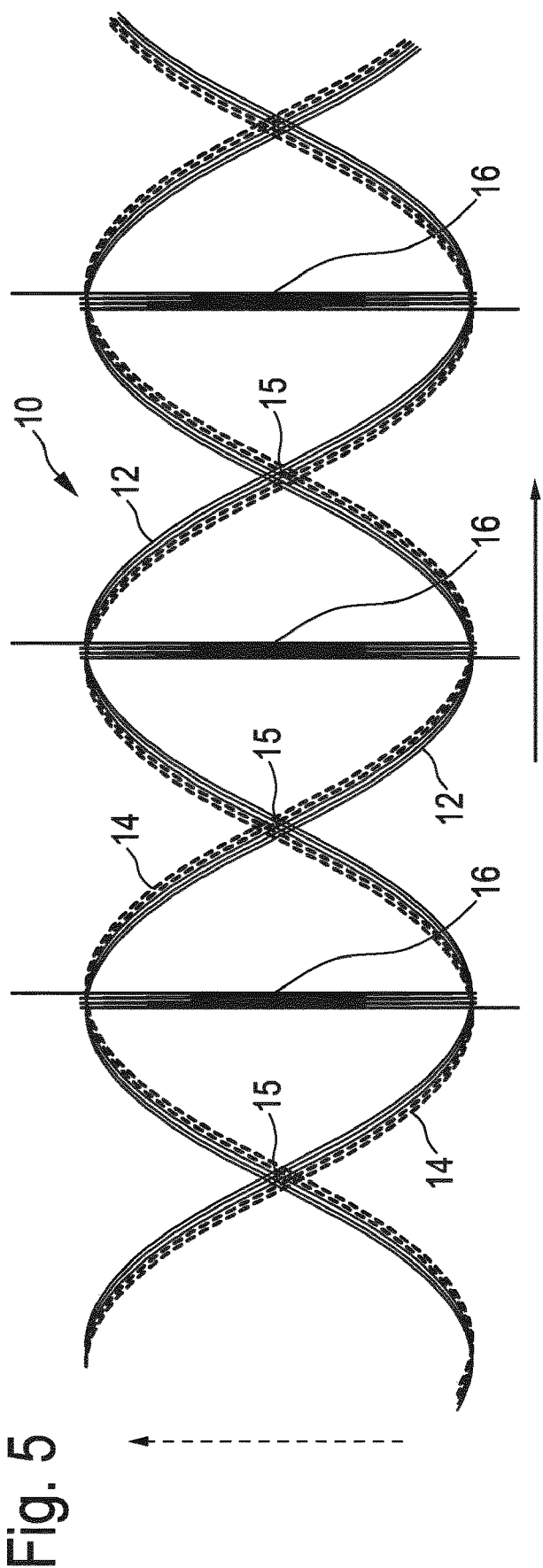

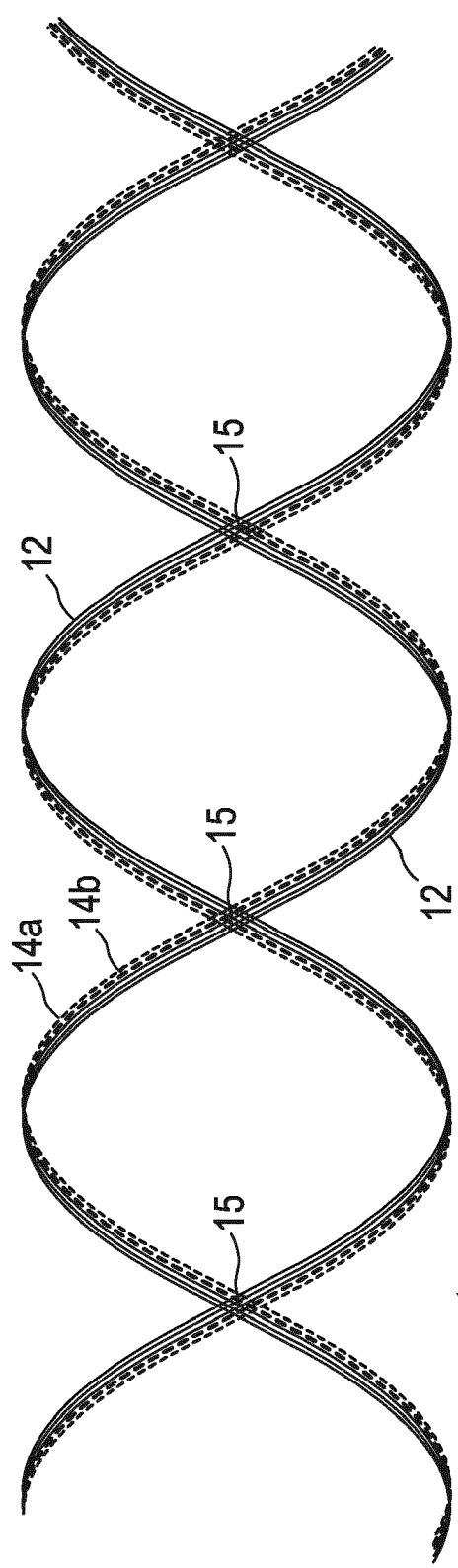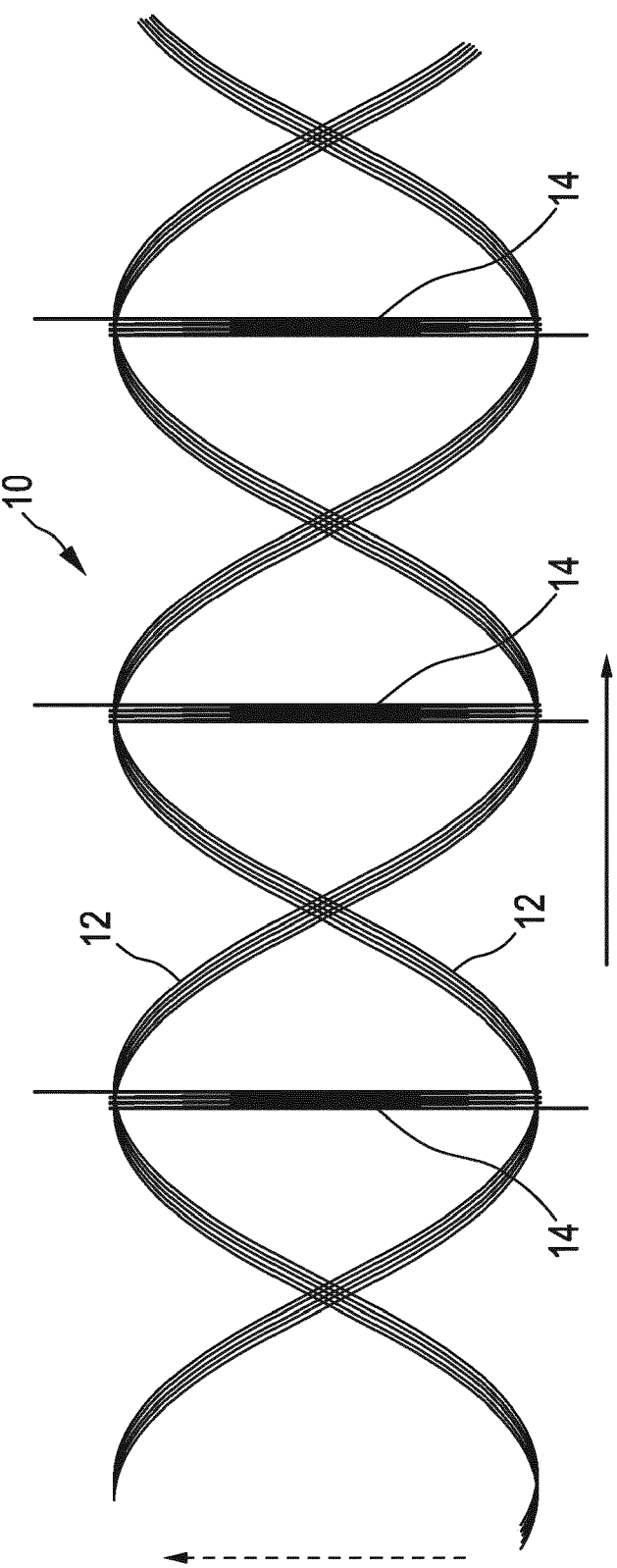

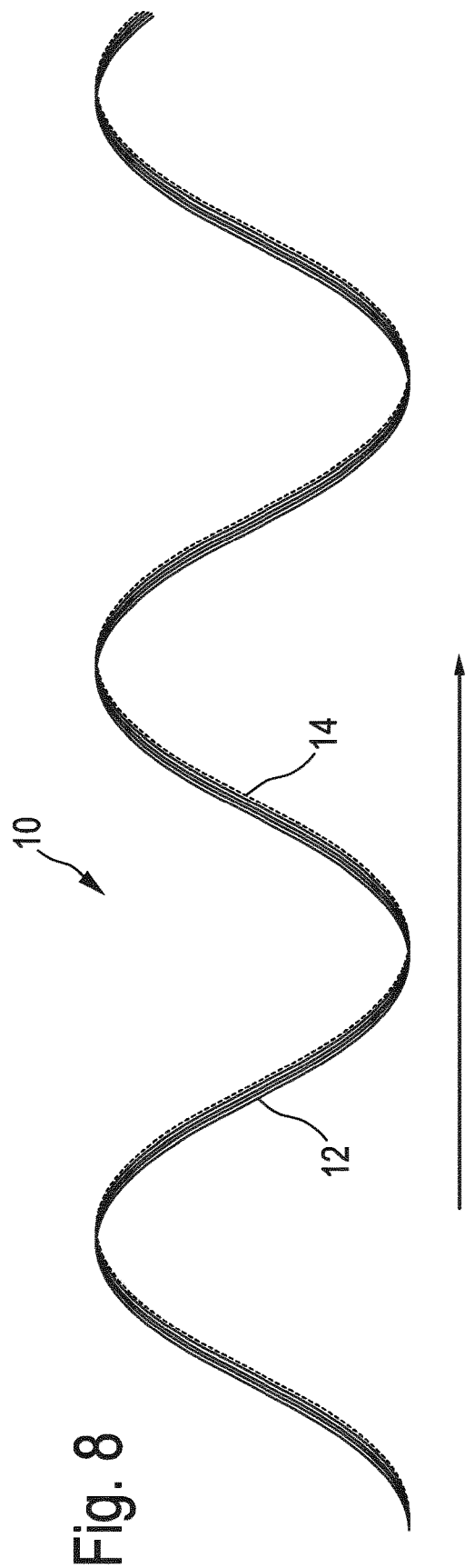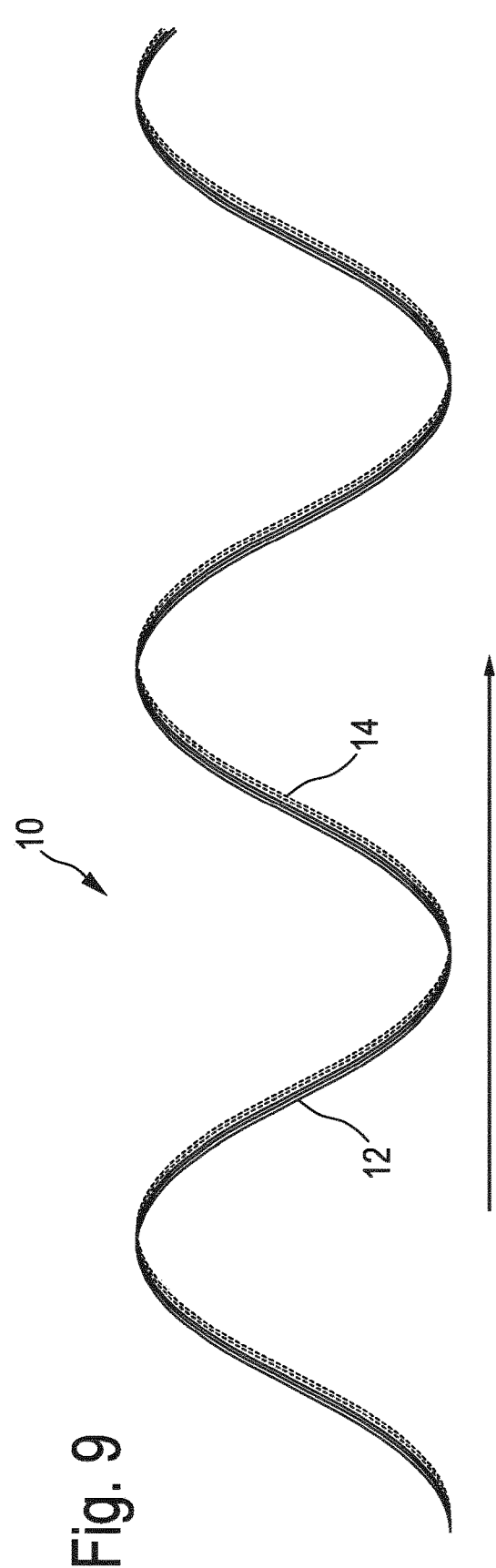

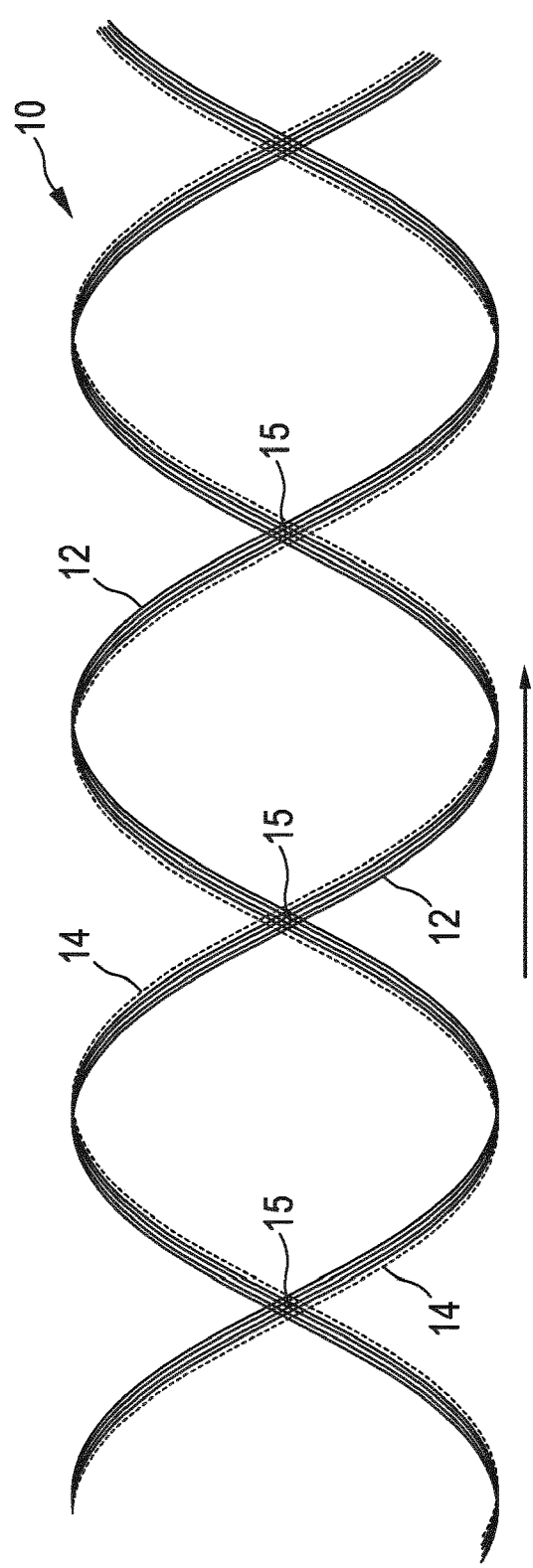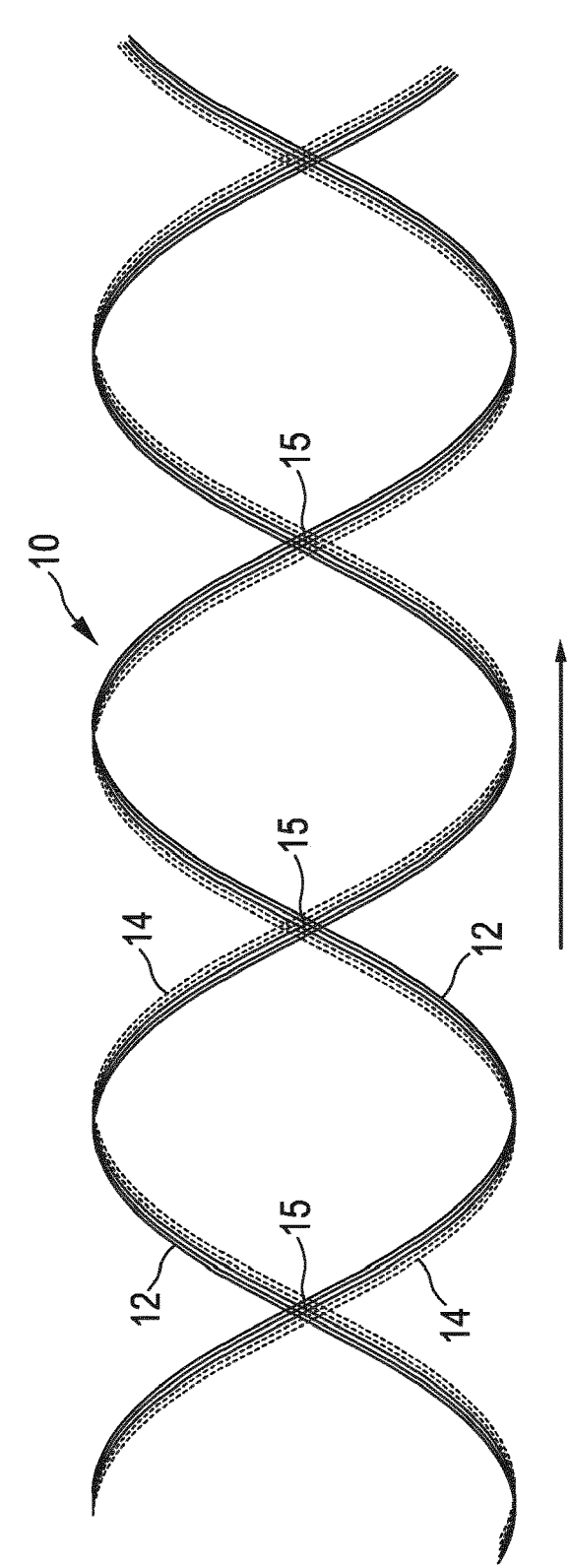

ENDOLUMINAL DEVICE

CROSS REFERENCE TO RELATED APPLICATION(S)

This application is the United States national phase entry of International Application No. PCT/EP2017/051531, filed Jan. 25, 2017, the content of which is incorporated by reference herein in its entirety.

FIELD

The invention relates to endoluminal devices, preferably useful in the treatment of stenosis and preventing restenosis disorders, methods for their manufacture and to surgical systems or kits.

BACKGROUND

Tubular organs and structures such as blood vessels are prone to stenosis, i.e. narrowing or constriction of the lumen. A stenosis can be caused by a variety of traumatic or organic disorders and symptoms can range from mild irritation and discomfort to paralysis and death. Treatment is site specific and dependent on the nature and extent of the stenosis.

For treating a stenosis in a blood vessel or heart valve, stents are typically applied. Stents reinforce body vessels and prevent restenosis following angioplasty in the vascular system.

Stents physically hold open and, if desired, expand the wall of the passage way. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location.

As an example, an endovascular stent may be inserted into a blood vessel during angioplasty, and is designed to prevent early collapse of a vessel that has been weakened or damaged by angioplasty. Insertion of endovascular stents has been shown to reduce negative remodeling of the vessel while healing of the damaged vessel wall proceeds over a period of months.

During the healing process, inflammation caused by angioplasty and stent device injury often causes smooth muscle cell proliferation and regrowth inside the stent, thus partially closing the flow channel, and thereby reducing or eliminating the beneficial effect of the angioplasty/stenting procedure. This process is called restenosis. Blood clots may also form inside of the newly implanted stent due to the thrombotic nature of the stent surfaces, even when biocompatible materials are used to form the stent. While large blood clots may not form during the angioplasty procedure itself or immediately post-procedure, due to the current practice of injecting powerful anti-platelet drugs into the blood circulation, some thrombosis is always present, at least on a microscopic level on stent surfaces, and it is supposed to play a significant role in the early stages of restenosis by establishing a biocompatible matrix on the surfaces of the stent where upon smooth muscle cells may subsequently migrate in and proliferate.

Stents can be of a permanent or temporary nature. Temporary stents may be advantageous, particular in cases of recurrent vessel narrowing in which it is desirable to insert a subsequent stent at or near the site of initial stent placement, or where a stent is needed only temporarily to counteract post-surgical swelling that may cause obstruction of a bodily lumen.

Stents made of a biodegradable material such as polylactide are known from EP 2 647 394 A2, EP 2 647 484 A1, WO 2000/074744 A1, WO 2007/139668 A2, EP 2 559 408 A2, US 2013/0317590 A1, WO 2007/126598 A2 and EP 2 465 551 A2.

Biodegradable polymeric stents often exhibit good stiffness which results in a long-term patency rate. On the other hand, these stents principally suffer from an increased recoil risk. Recoil refers to the percentage by which the diameter of a stent decreases from its expanded diameter (e.g. when a balloon is inflated at a nominal pressure) to its relaxed diameter (e.g. when a balloon is retrieved from the stent).

Further, biodegradable polymeric stents may expose an insufficient adhesion to a delivery catheter which may impede a medically correct placement of the stents. In case of stents made of polylactide, there is typically only a time slot of around 3 minutes for the surgeon to deliver and place the stents in a bodily lumen portion to be treated.

Stents formed from a magnesium alloy are known from WO 2013/052856 A2, WO 2013/024124 A1, WO 2011/117298 A1 and EP 1 632 255 A2. These stents exhibit superior mechanical properties in comparison to biodegradable polymeric stents. However, stents of magnesium alloy have their limitations with respect to a long-term patency rate. In that regard, mere administration of anti-proliferative agents is not suited to compensate for that shortcoming.

Thus, there remains a clinical need for devices which circumvent the disadvantages associated with common stents. In particular, there is a specific need of devices which on the one hand minimize the risk of recoil but on the other hand ensure a long-term patency rate.

SUMMARY

Thus, the object underlying the present invention is to provide an endoluminal device which properly addresses the afore-mentioned need.

The object is solved by endoluminal devices, methods for their manufacture and surgical systems or kits as defined in the description.

According to a first aspect, the invention relates to an endoluminal device, preferably for the treatment of stenosis and/or for preventing restenosis disorders. Thus, the endoluminal device is preferably a stent.

The endoluminal device comprises at least one composite yarn, i.e. one composite yarn or a plurality of composite yarns.

The at least one composite yarn comprises at least one polymer yarn, i.e. one polymer yarn or a plurality of polymer yarns, and at least one alloy wire, i.e. one alloy wire or a plurality of alloy wires.

The at least one polymer yarn comprises or consists of a polymer, in particular a biodegradable polymer.

Preferably, the polymer exhibits a slower biodegradation rate than the alloy of the at least one alloy wire. Thus, the alloy of the at least one alloy wire preferably increases the endoluminal device's mechanical stability during an initial and medium-term stage, in particular during storage (e.g. when crimped onto a delivery catheter) during implantation and in particular during a couple of months after implantation, while the polymer of the at least one polymer yarn advantageously facilitates a long-term support of the treated body lumen portion, and thus is advantageously responsible for a long-term patency rate. Preferably, the polymer of the at least one polymer yarn has a biodegradation rate of 1 to 3 years.

The polymer is preferably selected from the group consisting of polylactide, polyglycolide, poly(3-hydroxybutyrate), poly(4-hydroxybutyrate), polycaprolactone, poly(trimethylene carbonate) and a blend, i.e. mixture, of at least two of said polymers.

Further, the polymer is preferably a copolymer. More preferably, the copolymer comprises or consists of repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units.

Further, the polymer may be any combination of at least two of the afore-mentioned polymers and copolymers, respectively.

The at least one alloy wire comprises or consists of an alloy, typically a biocompatible alloy.

Further, the alloy may be a biodegradable, a partially biodegradable or a non-biodegradable alloy. Preferably, the alloy of the at least one alloy wire is a biodegradable alloy. More preferably, the alloy of the at least one alloy wire exhibits a faster biodegradation rate than the polymer of the alt least one polymer yarn. Due to a preferably permanent biodegradation of the alloy, a continuously increasing organ apposition, in particular blood vessel apposition, preferably artery apposition, can be accomplished due to an increasing expansion of the polymer of the at least one polymer yarn into the wall containing the bodily lumen. In particular, the alloy of the at least one alloy wire may have a biodegradation rate of 1 to 4 months.

Preferably, the alloy is selected from the group consisting of magnesium alloy, zinc alloy, iron alloy, cobalt-chromium alloy and a combination of at least two of said alloys. In particular, the iron alloy may be an alloyed stainless steel.

The invention is particularly featured by the following advantages:
  The endoluminal device according to the present invention combines the advantages of conventional metallic stents, in particular magnesium alloy stents, and biodegradable polymeric stents, in particular stents of polylactide.
  Due to the at least one alloy wire, the endoluminal device according to the present invention advantageously exhibits mechanical properties of a metallic stent such as radial strength and fracture toughness. Thus, a recoil or collapse risk can be minimized, in particular during an initial stage, e.g. after removal of a delivery device, preferably after deflation of a balloon catheter.
  Further, the at least one alloy wire advantageously facilitates sufficient attachment of the endoluminal device to a delivery instrument, in particular to a balloon of a balloon catheter, before and during implantation. Thus, delivery of the endoluminal device to a target lesion is made more convenient, resulting in a better handling for the surgeon and a higher safety for the patient.
  In case of biodegradable alloys, biodegradation rate by corrosion of the at least one alloy wire can be specifically adjusted by the nature, in particular composition, of the alloy.
  The at least one polymer yarn advantageously exhibits sufficient stiffness and strength resulting in a long-term patency rate which is highly desirable under medical point of views.
  Further advantages may arise if the polymer of the at least one polymer yarn is transferred into a memory shape condition, which may also contribute to a long-term patency rate. This does in particular apply if the polymer is polycaprolactone and/or poly(trimethylene carbonate).

The term "endoluminal device" as used according to the present invention refers to an artificial device that is adapted or configured to be implanted in a bodily lumen, in particular vascular lumen, preferably a venous or arterial lumen, more preferably an arterial lumen. Thus, the endoluminal device, according to the present invention, may also be denoted as an endoluminal implant. Most preferably, the endoluminal device according to the present invention is a stent, in particular a endovenous or endoarterial stent, preferably an endoarterial stent.

The term "lumen" as used according to the present invention refers to a cavity of an organ, in particular of a tubular organ such as a blood vessel, in particular vein or artery, more preferably artery.

The term "bodily lumen" as used according to the present invention means a lumen within a human or animal body. Preferably, the term "bodily lumen" as used according to the present invention means a vascular lumen, in particular a venous or an arterial lumen, more preferably an arterial lumen.

The term "biodegradable" means according to the present invention partial or complete disintegration or degradation upon exposure to bodily fluids, preferably blood or tissue, and can include resorption and/or absorption and/or decomposition and/or elimination by a patient's body.

The term "copolymer" as used according to the present invention defines a polymer which is composed of at least two different repeating monomeric units. Thus, a copolymer according to the present invention can be, by way of example, a bipolymer or terpolymer.

The term "blend" as used according to the present invention defines a mixture comprising or consisting of at least two different polymers.

The term "alloy" as used according to the present invention defines a mixture of at least two different metals or of a metal and another element.

The term "yarn" as used according to the present invention defines, in particular in accordance with DIN 60900, a long and thin, in particular a long, thin and textile, entity comprising or consisting of one fibre or of a plurality of fibres.

The term "composite yarn" as used according to the present invention defines a yarn comprising or consisting of at least two differently embodied long and thin entities, in particular long, thin and textile entities. The entities are preferably at least one polymer yarn and/or at least one alloy wire.

The term "covered yarn" as used according to the present invention defines a yarn comprising or consisting of at least two differently embodied long and thin entities, in particular long, thin and textile entities, wherein at least one entity is covered by the at least one remaining entity. The entities are preferably at least one polymer yarn and/or at least one alloy wire.

The term "wrapped yarn" as used according to the present invention defines a yarn comprising or consisting of at least two differently embodied long and thin entities, in particular long, thin and textile entities, wherein at least one entity is wrapped, in particular spirally wrapped, preferably helically wrapped, by the at least one remaining entity. The entities are preferably at least one polymer yarn and/or at least one alloy wire.

In a preferred embodiment, the at least one polymer yarn comprises or consists of polylactide and the at least one alloy wire preferably comprises or consists of an alloy selected from the group consisting of magnesium alloy, zinc alloy, iron alloy, cobalt-chromium alloy and a combination of at least two of said alloys.

Preferably, the polylactide is selected from the group consisting of poly(L-lactide), poly(D,L-lactide), poly(D-lactide) and a blend of at least two of said polymers. More preferably, the polylactide is poly(L-lactide).

It is especially preferred if the at least one polymer yarn comprises or consists of polylactide, in particular poly(L-lactide), and the at least one alloy wire comprises or consists of magnesium alloy.

Further, the at least one polymer yarn may comprise or consist of polyglycolide and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of poly(3-hydroxybutyrate) and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of poly(4-hydroxybutyrate) and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of polycaprolactone and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of poly(trimethylene carbonate) and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of a copolymer and the at least one alloy wire may comprise or consist of an alloy selected from the group consisting of magnesium alloy, zinc alloy, iron alloy, cobalt-chromium alloy and a combination of at least two of said alloys.

Preferably, the copolymer comprises or consists of repeating lactide units. The lactide units may be L-lactide units and/or D-lactide units. Preferably, the lactide units are L-lactide units.

More preferably, the copolymer is selected from the group consisting of poly(L-lactide-co-glycolide), poly(D,L-lactide-co-glycolide), poly(D-lactide-co-glycolide), poly(L-lactide-co-caprolactone), poly(D,L-lactide-co-caprolactone), poly(D-lactide-co-caprolactone), poly(3-hydroxybutyrate-co-3-hydroxyvalerate), poly(3-hydroxybutyrate-co-4-hydroxybutyrate), poly(3-hydroxybutyrate-co-3-hydroxyoctanoate) and a blend of at least two of said copolymers.

Further, the at least one polymer yarn may comprise or consist of a copolymer comprising or consisting of repeating glycolide units and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of a copolymer comprising or consisting of repeating 6-hydroxyhexanoic acid units and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of a copolymer comprising or consisting of repeating 3-hydroxybutyrate units and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of a copolymer comprising or consisting of repeating 4-hydroxybutyrate units and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of a copolymer comprising or consisting of repeating trimethylencarbonate units and the at least one alloy wire may comprise or consist of an alloy selected from the group consisting of magnesium alloy, zinc alloy, iron alloy, cobalt-chromium alloy and a combination of at least two of said alloys.

Further, the at least one polymer yarn may comprise or consist of any blend of at least two polymers and copolymers, respectively as mentioned in the preceding embodiments.

Preferably, the at least one polymer yarn comprises or consists of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and combinations of at least two of said monomer units, and a blend of at least two of said polymers and the at least one alloy wire preferably comprises or consists of a magnesium alloy.

The term "magnesium alloy" as used according to the present invention preferably defines a mixture of magnesium, typically as the main constituent, with at least one further metal. The at least one further metal may be selected from the group consisting of aluminium, bismuth, titan, wolfram cadmium, palladium, rare earth element, gadolinium, dysprosium, neodymium, europium, yttrium, iron, thorium, calcium, strontium, zirconium, lithium, rubidium, manganese, nickel, lead, silver, cobalt, chromium, silicon, tin, calcium, antimony, copper, zinc and an alloy of at least two of said metals.

More preferably, the term "magnesium alloy" as used according to the present invention defines an alloy which along magnesium, in particular as the main constituent, comprises at least one further metal which is selected from the group consisting of calcium, zirconium, yttrium, dysprosium, neodymium, europium and a combination of at least two of said metals.

In particular, the magnesium alloy may contain the following components based on the total weight of the alloy:
5.0% by weight to 25.5% by weight dysprosium
0.01% by weight to 5.0% by weight neodymium and/or europium
0.1% by weight to 3.0% by weight zinc
0.1% by weight to 2.0% by weight zirconium
balance to 100% by weight magnesium.

Further, the magnesium alloy may be selected from the group consisting of magnesium alloy comprising (—along magnesium —) yttrium, neodymium, zinc and zirconium, magnesium alloy comprising (—along magnesium —) yttrium, europium, zinc and zirconium, magnesium alloy comprising (—along magnesium —) dysprosium, neodymium, zinc and zirconium, magnesium alloy comprising (—along magnesium-) dysprosium, europium, zinc and zirconium, magnesium alloy comprising (—along magnesium —) calcium, neodymium, zinc and zirconium, magnesium alloy comprising (—along magnesium —) calcium, europium, zinc and zirconium and a combination of at least two of said alloys.

Further, the magnesium alloy may be an alloy which is commercially available under the abbreviation "AZ31b". This magnesium alloy contains 2.5 percent by weight to 3.5 percent by weight of aluminium, at most 0.2 percent by weight of manganese, 0.6 percent by weight to 1.4 percent by weight of zinc, at most 0.005 percent by weight of iron, at most 0.05 percent by weight of copper, at most 0.10 percent by weight of silicon, at most 0.04 percent by weight of calcium and at most 0.005 percent by weight of nickel, each in relation to the total weight of the magnesium alloy.

Further, the magnesium alloy may be an alloy which is commercially available under the abbreviation "WE43". This magnesium alloy contains 3.7 to 4.3 percent by weight of yttrium, 2.4 to 4.4 percent by weight of rare earths and 0.4 percent by weight of zirconium, each in relation to the total weight of the magnesium alloy.

Further, the at least one polymer yarn may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of a zinc alloy.

The term "zinc alloy" as used according to the present invention preferably defines a mixture of zinc, typically as the main constituent, with at least one further metal. The at least one further metal may be selected from the group consisting of magnesium, aluminium, bismuth, titan, wolfram, cadmium, palladium, rare earth element, gadolinium, dysprosium, neodymium, europium, yttrium, iron, thorium, calcium, strontium, zirconium, lithium, rubidium, manganese, nickel, lead, silver, cobalt, chromium, silicon, tin, calcium, antimony, copper and an alloy of at least two of said metals.

More preferably, the term "zinc alloy" as used according to the present invention defines an alloy which along zinc, in particular as the main constituent, comprises at least one further metal which is selected from the group consisting of iron, lithium, calcium, magnesium, a rare earth element (such as gadolinium and/or dysprosium and/or neodymium and/or europium and/or yttrium) and a combination of at least two of said metals.

In particular, the zinc alloy may be selected from the group consisting of zinc alloy comprising (—along zinc —) iron and lithium, zinc alloy comprising (—along zinc —) iron and calcium, zinc alloy comprising (—along zinc —) iron and magnesium and a combination of at least two of said alloys.

Further, the at least one polymer yarn may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of an iron alloy.

The term "iron alloy" as used according to the present invention preferably defines a mixture of iron, typically as the main constituent, with at least one further metal. The at least one further metal may be selected from the group consisting of magnesium, aluminium, bismuth, titan, wolfram, cadmium, palladium, rare earth element, gadolinium, dysprosium, neodymium, europium, yttrium, thorium, calcium, strontium, zirconium, lithium, rubidium, manganese, nickel, lead, silver, cobalt, chromium, silicon, tin, calcium, antimony, copper, zinc and an alloy of at least two of said metals.

More preferably, the term "iron alloy" as used according to the present invention defines an alloy which along iron, in particular as the main constituent, comprises at least one further metal which is selected from the group consisting of manganese, palladium, silicon and a combination of at least two of said metals. In particular, the iron alloy may—along iron—comprise manganese and/or palladium and/or silicon.

Further, the iron alloy as used according to the present invention may be an alloyed stainless steel. Preferably, the alloyed stainless steel comprises along iron, in particular as the main constituent, at least one further metal selected from the group consisting of chromium, nickel, platinum, molybdenum and a combination of at least two of said alloys. In particular, the alloyed stainless steel may—along iron—comprise chromium and nickel and/or platinum and molybdenum, in particular chromium and nickel or platinum and molybdenum. For example, the alloyed stainless steel may be a steel of type AISI 316 L.

Accordingly, the at least one polymer yarn may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of an alloyed stainless steel.

Further, the at least one polymer yarn may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of a cobalt-chromium alloy.

The term "cobalt-chromium alloy" as used according to the present invention preferably defines a mixture of at least cobalt and chromium, and optionally with at least one further metal. The optional at least one further metal may be selected from the group consisting of aluminium, bismuth, titan, wolfram, cadmium, palladium, rare earth element, gadolinium, dysprosium, neodymium, europium, yttrium, iron, thorium, calcium, strontium, zirconium, lithium, rubidium, manganese, nickel, lead, silver, silicon, tin, calcium, antimony, copper, zinc and an alloy of at least two of said metals.

More preferably, the term "cobalt-chromium alloy" as used according to the present invention defines an alloy which along cobalt and chromium, in particular as the main constituents, comprises at least one further metal which is selected from the group consisting of nickel, tungsten (wolfram) and a combination of at least two of said metals. For example, the cobalt-chromium alloy may be a cobalt-chromium alloy according to ASTM F90 or ISO 5832-5.

Further, the at least one alloy wire may comprise or consist of any combination of at least two alloys as mentioned in the preceding embodiments.

In an especially preferred embodiment, the at least one polymer yarn comprises or consists of polylactide, in particular poly(L-lactide), and the at least one alloy wire comprises or consists of a magnesium alloy. With respect to further details, in particular in terms of polylactide and magnesium alloy, reference is made in its entirety to previous description. The features and advantages disclosed therein apply accordingly.

Further, the at least one polymer yarn may comprise or consist of a copolymer comprising or consisting of repeating lactide units, in particular repeating L-lactide units, and the at least one alloy wire may comprise or consist of a magnesium alloy. With respect to further details, in particular in terms of the copolymer and magnesium alloy, reference is made in its entirety to previous description. The features and advantages disclosed therein apply accordingly.

Further, the at least one polymer yarn may have a rounded, in particular circular or oval, cross-section.

Alternatively, the at least one polymer yarn may have a non-circular cross-section such as a trigonal, square, quadrangular, trapezoidal, rhombic, pentagonal, hexagonal or star-like cross-section.

A circular or triangular cross-section of the at least one polymer yarn is especially advantageous, since both types of cross-sections allow for a better embedding of the endoluminal device, in a wall surrounding a body lumen, and thus facilitate a secure and in particular long-term positioning of the endoluminal device within a bodily lumen.

Further, the at least one polymer yarn may exhibit a diameter from 5 μm to 300 μm, in particular 10 μm to 200 μm, preferably 15 μm to 150 μm Further, the at least one polymer yarn may exhibit a linear density from >0.01 tex [g/km] to 150 tex [g/km]tex, in particular 0.09 tex [g/km] to 100 tex [g/km], preferably 0.2 tex [g/km] to 75 tex [g/km].

Further, the at least one polymer yarn may exhibit a length from 5 mm to 9000 mm, in particular 8 mm to 7000 mm, preferably 10 mm to 5000 mm.

Further, the at least one polymer yarn may comprise or consist of (only) one polymer fibre. In other words, the at least one polymer yarn may be embodied as (only) one polymer fibre.

Further, the at least one polymer yarn may comprise or consist of a plurality of polymer fibres, in particular differently embodied polymer fibres, preferably in terms of length, cross-section, diameter, linear density, biodegradation rate, polymer and combinations thereof.

The at least one polymer yarn may in particular comprise or consist of 1 to 50, in particular 2 to 30, preferably 3 to 20, polymer fibres.

Further, the polymer fibres may exhibit a diameter from 0.5 μm to 300 μm, in particular 2 μm to 200 μm, preferably 5 μm to 150 μm.

Further, the polymer fibres may exhibit a linear density from less than 0.01 tex [g/km] to 150 tex [g/km], in particular 0.09 tex [g/km] to 100 tex [g/km], preferably 0.2 tex [g/km] to 75 tex [g/km].

Further, the polymer fibres may exhibit a length from 5 mm to 9000 mm, in particular 8 mm to 7000 mm, preferably 10 mm to 5000 mm.

Further, the polymer fibres may have a round, in particular circular or oval, cross-section.

Alternatively, the polymer fibres may have a non-circular cross-section, such as a trigonal, square, quadrangular, trapezoidal, rhombic, pentagonal, hexagonal or stark-like cross-section.

Advantageously, the stiffness and strength, and thus in particular a long-term patency rate of the endoluminal device, can be purposefully controlled by the at least one polymer yarn's parameters and or by the respective parameters of the at least one polymer yarn's fibre(s) as described in the preceding embodiments.

Further, the at least one polymer yarn may comprise a biodegradation-retarding agent, in particular rubidium, rubidium alloy or a rubidium compound. Thus, in case of a biodegradable alloy for the at least one alloy wire, biodegradation rate of the at least one alloy wire can be purposefully influenced.

Further the at least one polymer yarn may be embodied as one polymer yarn. In other words, the at least one composite yarn may comprise (only) one polymer yarn. It goes without saying that the features and advantages disclosed in the previous description in respect of the at least one polymer yarn do apply accordingly, if the at least one polymer yarn is embodied as (only) one polymer yarn.

Further, the at least one polymer yarn may correspond to a plurality of polymer yarns, in particular to a plurality of differently embodied polymer yarns. In other words, the at least one composite yarn may comprise a plurality of polymer yarns, in particular a plurality of differently embodied polymer yarns. Preferably, the polymer yarns are differently embodied in terms of length, cross-section, diameter, biodegradation rate, structure, polymer, additivation of the polymer, number of polymer fibres or combinations thereof. It goes without saying that the features and advantages disclosed in the previous description in respect of the at least one polymer yarn do apply accordingly, in particular to each polymer yarn or only a part of the polymer yarns, if the at least one polymer yarn is defined as a plurality of polymer yarns. Thus, as regards length, diameter, cross-section, biodegradation rate, structure, polymer, additivation of the polymer, and number of polymer fibres, reference is made in its entirety to the previous description.

Further, the at least one alloy wire of the at least one composite yarn may have a round, in particular circular or oval, cross-section.

Alternatively, the at least one alloy wire may have a non-circular cross-section, in particular a trigonal, square, quadrangular, trapezoidal, rhombic, pentagonal, hexagonal or star-like cross-section.

A circular or triangular cross-section of the at least one alloy wire is especially advantageous, since both types of cross-sections allow for a better embedding of the endoluminal device, in a wall surrounding a body lumen, and thus facilitate a secure and in particular long-term positioning of the device within a bodily lumen.

Further, the at least one alloy wire may exhibit a diameter from 1 µm to 300 µm, in particular 5 µm to 200 µm, preferably 10 µm to 150 µm. Thus, in particular time-dependent mechanical characteristics in case of a biodegradable alloy, such as radial strength and/or fracture toughness, can be purposefully controlled.

Further, the at least one alloy wire may exhibit a length from 5 mm to 9000 mm, in particular 8 mm to 7000 mm, preferably 10 mm to 5000 mm.

Further, the at least one alloy wire may have a grain size from more than 12 to 3, in particular more than 12 to 6, preferably more than 12 to 8, according to ASTM 112-12. The grain size disclosed in this paragraph advantageously allows deformation of the at least one alloy wire without destruction. Alternatively, the at least one alloy wire may be made of a monolithic grain size.

Further, the at least one wire may have a core-sheath structure. In other words, the at least one wire may comprise a core and a sheath, wherein the sheath surrounds or covers the core. The sheath may only partially or completely surround or cover the core. Principally, the core and/or sheath may comprise or consist of an alloy or a combination of at least two alloys as disclosed in the previous description. Thus, preferably, the core and/or sheath may comprise or consist of an alloy selected from the group consisting of magnesium alloy, zinc alloy, iron alloy, alloyed stainless steel, cobalt-chromium alloy and combinations of at least two of said alloys.

Preferably, the core comprises or consists of a biodegradable alloy and the sheath comprises or consists of a non-biodegradable alloy or slower biodegradable alloy, i.e. an alloy which exhibits a slower biodegradation rate than the alloy of the core. For example, the core may comprise or consist of a magnesium alloy, while the sheath may comprise or consist of a zinc alloy. Alternatively, the core may comprise or consist of a biodegradable alloy such as a magnesium alloy, while the sheath may comprise or consist of a non-biodegradable elementary metal such as titan or wolfram or compounds thereof. Thus, biodegradation of the core may be advantageously controlled, in particular retarded, and/or biocompatibility of the endoluminal device can be adjusted.

Further, the at least one alloy wire may be embodied as one alloy wire. In other words, the at least one composite yarn may comprise (only) one alloy wire. It goes without saying that the features and advantages disclosed in the previous description in respect of the at least one alloy wire do apply accordingly, if the at least one alloy wire is embodied as (only) one alloy wire.

Further, the at least one alloy wire may correspond to a plurality of alloy wires, in particular to a plurality of differently embodied alloy wires. In other words, the at least one composite yarn may comprise a plurality of alloy wires, in particular a plurality of differently embodied alloy wires.

Preferably, the alloy wires are differently embodied in terms of length, cross-section, diameter, biodegradation rate, structure, alloy or combinations thereof. It goes without saying that the features and advantages disclosed in the previous description in respect of the at least one alloy wire do apply accordingly, in particular to each alloy wire or only a part of the alloy wires, if the at least one alloy wire is defined as a plurality of alloy wires. Thus, as regards length, diameter, cross-section, biodegradation rate, structure and alloy, reference is made in its entirety to the previous description.

In case of a biodegradable alloy, under stability aspects a plurality of alloy wires has the advantage that a progressive biodegradation of one alloy wire may be compensated by at least one further alloy wire, in particular by several further alloy wires.

For example, the at least one composite yarn may comprise or consist of 1 to 40, in particular 2 to 30, preferably 3 to 20, alloy wires.

Further, the at least one alloy wire may comprise or consist of at least two alloy wires which are differently embodied in terms of diameter. For example, the at least one alloy wire may comprise a first alloy wire having a diameter of 30 µm and a second alloy wire having a diameter of 50 µm.

Further, the at least one alloy wire may comprise at least two alloy wires which are differently embodied in terms of the alloy. For example, the at least one alloy wire may comprise a first alloy wire comprising or consisting of a biodegradable alloy and a second alloy wire comprising or consisting of a non-biodegradable or a slower biodegradable alloy, i.e. an alloy which exhibits a slower biodegradation rate than the alloy of the first alloy wire. Preferably, the biodegradable alloy is a magnesium alloy. The non-biodegradable or slower biodegradable alloy is preferably a zinc alloy. With respect to further features and advantages of the magnesium alloy and/or zinc alloy, reference is made in its entirety to the previous description.

In a further embodiment, the at least one composite yarn is embodied as at least one covered yarn, i.e. as one covered yarn or as a plurality of covered yarns.

Preferably, the at least one composite yarn, in particular the at least one covered yarn, is embodied as at least one wrapped yarn, i.e. as one wrapped yarn or as a plurality of wrapped yarns.

Principally, the at least one alloy wire may be surrounded, in particular wrapped, preferably spirally wrapped, more preferably helically wrapped, by the at least one polymer yarn.

In particular, per metre of the at least one composite yarn, preferably per metre of the at least one wrapped yarn, the at least one alloy wire may be wrapped, in particular spirally wrapped, preferably helically wrapped, at least one time, in particular at least 500 times, preferably at least 1000 times, by the at least one polymer yarn.

Preferably, the at least one polymer yarn is surrounded, in particular wrapped, preferably spirally wrapped, more preferably helically wrapped, by the at least one alloy wire. Thus, an especially high stability towards an endoluminal wall of a body vessel, in particular venous or arterial blood vessel, can be exercised. This in particular helps to avoid restenosis of a blood vessel.

In particular, per metre of composite yarn, preferably per metre of the at least one wrapped yarn, the at least one polymer yarn may be wrapped, in particular spirally wrapped, preferably helically wrapped, by the at least one alloy wire at least one time, in particular at least 500 times, preferably at least 1000 times.

Further, the at least one composite yarn may be arranged in a longitudinal and/or in a circumferential direction of the endoluminal device.

In particular, the at least one composite yarn may be arranged in a circumferential direction of the endoluminal device or may surround the endoluminal device along its circumference.

Preferably, the at least one composite yarn may be embodied as an enlacement (loop) which is preferably arranged in a circumferential direction of the endoluminal device or which preferably surrounds the endoluminal device along its circumference. Thus, the radial stiffness and/or suspension of the endoluminal device can be significantly increased. In case of a plurality of composite yarns, it is preferred if each composite yarn is embodied as an enlacement (loop) which is preferably arranged in a circumferential direction of the endoluminal device or which preferably surrounds the endoluminal device along its circumference.

Further, the at least one composite yarn may comprise or consist of one polymer yarn and one alloy wire. It goes without saying that the features and advantages disclosed in the previous description in respect of the at least one polymer yarn and the at least one alloy wire of the at least one composite yarn do apply accordingly, if the at least one polymer yarn is embodied as one polymer yarn and the at least one alloy wire is embodied as one alloy wire.

Further, the at least one composite yarn may comprise a plurality of polymer yarns and one alloy wire. It goes without saying that the features and advantages disclosed in the previous description in respect of the at least one polymer yarn and the at least one alloy wire of the at least one composite yarn do apply accordingly, in particular to each polymer yarn or only a part of the polymer yarns, if the at least one polymer yarn is embodied as a plurality of polymer yarns and the at least one alloy wire is embodied as one alloy wire.

Further, the at least one composite yarn may comprise one polymer yarn and a plurality of alloy wires. It goes without saying that the features and advantages disclosed in the previous description in respect of the at least one polymer yarn and the at least one alloy wire of the at least one composite yarn do apply accordingly, in particular to each alloy wire or only a part of the alloy wires, if the at least one polymer yarn is embodied as one polymer yarn and the at least one alloy wire is embodied as plurality of alloy wires.

Further, the at least one composite yarn may comprise a plurality of polymer yarns and a plurality of alloy wires. It goes without saying that the features and advantages disclosed in the previous description in respect of the at least one polymer yarn and the at least one alloy wire of the at least one composite yarn do apply accordingly, in particular to each polymer yarn or only a part of the polymer yarns and/or to each alloy wire or only a part of the alloy wires, if the at least one polymer yarn is embodied as a plurality of polymer yarns and the at least one alloy wire is embodied as plurality of alloy wires.

Further, the at least one composite yarn may be one composite yarn. In other words, the endoluminal device may (only) comprise one composite yarn. It goes without saying that the features and advantages disclosed in the previous description in respect of the at least one composite yarn do apply accordingly, if the at least one composite yarn is embodied as (only) one composite yarn.

Further, the at least one composite yarn may correspond to a plurality of composite yarns, in particular to a plurality of differently embodied composite yarns. In other words, the endoluminal device may comprise a plurality of composite yarns, in particular a plurality of differently embodied composite yarns. Preferably, the composite yarns are differently embodied in terms of length, structure, cross-section of the at least one polymer yarn and/or the at least one alloy wire, diameter of the at least one polymer yarn and/or the at least one alloy wire, biodegradation rate of the at least one polymer yarn and/or the at least one alloy wire, alloy of the at least one alloy wire, number of alloy wires, polymer of the at least one polymer yarn, number of polymer yarns and/or fibres thereof, or combinations thereof. It goes without saying that the features and advantages disclosed in the previous description in respect of the at least one composite yarn do apply accordingly, in particular to each composite yarn or only a part of the composite yarns, if the at least one composite yarn is defined as a plurality of composite yarns. Thus, as regards length, structure, cross-section of the at least one polymer yarn and/or the at least one alloy wire, diameter of the at least one polymer yarn and/or the at least one alloy wire, biodegradation rate of the at least one polymer yarn and/or the at least one alloy wire, alloy of the at least one alloy wire, number of alloy wires, polymer of the at least one polymer yarn and number of polymer yarns and/or fibres thereof, reference is made in its entirety to the previous description.

Preferably, the endoluminal device comprises a plurality of composite yarns which are differently embodied in terms of diameter of the at least one alloy wire. For example, the endoluminal device may comprise a composite yarn comprising at least one alloy wire having a diameter of 30 μm and a further a composite yarn comprising at least one alloy wire having a diameter of 50 μm.

In a further embodiment, the endoluminal device additionally comprises at least one further polymer yarn, i.e. one further polymer yarn or a plurality of further polymer yarns.

The at least one further polymer yarn may have a rounded, in particular circular or oval, cross-section.

Alternatively, the at least one further polymer yarn may have a non-circular cross-section such as a trigonal, square, quadrangular, trapezoidal, rhombic, pentagonal, hexagonal or star-like cross-section.

A circular or triangular cross-section of the at least one further polymer yarn is especially advantageous, since both types of cross-sections allow for a better embedding of the endoluminal device, in a wall surrounding a body lumen, and thus facilitate a secure and in particular long-term positioning of the device within a bodily lumen.

Further, the at least one further polymer yarn may exhibit a diameter from 5 μm to 300 μm, in particular 10 μm to 200 μm, preferably 15 μm to 150 μm Further, the at least one further polymer yarn may exhibit a linear density from >0.01 tex [g/km] to 150 tex [g/km]tex, in particular 0.09 tex [g/km] to 100 tex [g/km], preferably 0.2 tex [g/km] to 75 tex [g/km].

Further, the at least one further polymer yarn may exhibit a length from 5 mm to 9000 mm, in particular 8 mm to 7000 mm, preferably 10 mm to 5000 mm.

Further, the at least one further polymer yarn may comprise or consist of (only) one polymer fibre. In other words, the at least one further polymer yarn may be embodied as (only) one polymer fibre.

Further, the at least one further polymer yarn may comprise or consist of a plurality of polymer fibres, in particular differently embodied polymer fibres, preferably in terms of cross-section, diameter, linear density, biodegradation rate, polymer, number of fibres and combinations thereof.

As regards further features of the polymer fibre(s) of the at least one further polymer yarn and advantages related therewith, in particular in terms of length, number, cross-section, diameter, linear density, polymer, additivation of the polymer and combinations thereof, reference is made in its entirety to the respective embodiments regarding the polymer fibre(s) of the at least one polymer yarn of the at least one composite yarn disclosed in the previous description, which do apply accordingly.

Further, the at least one further polymer yarn may be embodied as one further polymer yarn. In other words, the endoluminal device may comprise (only) one further polymer yarn. It goes without saying that the features and advantages disclosed in the previous description in respect of the at least one further polymer yarn do apply accordingly, if the at least one further polymer yarn is embodied as (only) one polymer yarn.

Further, the at least one further polymer yarn may correspond to a plurality of polymer yarns, preferably to a plurality of differently embodied polymer yarns. In other words, the endoluminal device may comprise a plurality of further polymer yarns. Preferably, the further polymer yarns are differently embodied in terms of length, cross-section, diameter, biodegradation rate, structure, polymer, additivation of the polymer, number of polymer fibres or combinations thereof. It goes without saying that the features and advantages disclosed in the previous description in respect of the at least one further polymer yarn do apply accordingly, in particular to each further polymer yarn or only to a part of the further polymer yarns, if the at least one further polymer yarn is embodied as a plurality of further polymer yarns. Thus, as regards length, diameter, cross-section, biodegradation rate, structure, polymer, additivation of the polymer, and number of polymer fibres, reference is made in its entirety to the previous description.

Preferably, the at least one further polymer yarn comprises or consists of the same polymer as the at least one polymer yarn of the at least one composite yarn.

More preferably, the at least one further polymer yarn comprises or consists of polylactide.

The polylactide is in particular selected from the group consisting of poly(L-lactide), poly(D,L-lactide), poly(D-lactide) and a blend of at least two of said polymers. More preferably, the polylactide is poly(L-lactide).

Further, the at least one further polymer yarn may comprise or consist of polyglycolide.

Further, the at least one further polymer yarn may comprise or consist of poly(3-hydroxybutyrate).

Further, the at least one further polymer yarn may comprise or consist of poly(4-hydroxybutyrate).

Further, the at least one further polymer yarn may comprise or consist of polycaprolactone.

Further, the at least one further polymer yarn may comprise or consist of poly(trimethylene carbonate).

Further, the at least one further polymer yarn may comprise or consist of a copolymer. Preferably, the copolymer comprises repeating lactide units. The lactide units may be L-lactide units and/or D-lactide units. Preferably, the lactide units are L-lactide units.

More preferably, the copolymer is selected from the group consisting of poly(L-lactide-co-glycolide), poly(D,L-lactide-co-glycolide), poly(D-lactide-co-glycolide), poly(L-lactide-co-caprolactone), poly(D,L-lactide-co-caprolactone), poly(D-lactide-co-caprolactone), poly(3-hydroxybutyrate-co-3-hydroxyvalerate), poly(3-hydroxybutyrate-co-4-hydroxybutyrate), poly(3-hydroxybutyrate-co-3-hydroxyoctanoate) and a blend of at least two of said copolymers.

Further, the at least one further polymer yarn may comprise or consist of a copolymer comprising or consisting of repeating glycolide units.

Further, the at least one further polymer yarn may comprise or consist of a copolymer comprising or consisting of repeating 6-hydroxyhexanoic acid units.

Further, the at least one further polymer yarn may comprise or consist of a copolymer comprising or consisting of repeating 3-hydroxybutyrate units.

Further, the at least one further polymer yarn may comprise or consist of a copolymer comprising or consisting of repeating 4-hydroxybutyrate units.

Further, the at least one further polymer yarn may comprise or consist of a copolymer comprising or consisting of repeating trimethylencarbonate units.

Further, the at least one further polymer yarn may comprise or consist of any blend of at least two polymers and copolymers, respectively as mentioned in the preceding embodiments.

In a further embodiment, the at least one composite yarn and/or the at least one further polymer yarn, in particular the at least one composite yarn and the at least one further polymer yarn, are connected to each other, in particular by means of a textile technique and/or by means of a material bonding engagement. The textile technique may be selected from the group consisting of weaving, knitting, braiding and a combination of at least two of said textile techniques. The material bonding engagement may be selected from the group consisting of gluing, welding (such as laser welding and/or electron beam welding), melting and a combination of at least two of said material bonding engagements.

In a further embodiment, the at least one composite yarn and/or the at least one further polymer yarn, preferably the at least one composite yarn and the at least one further polymer yarn, extend in spirals, in particular helices, along a longitudinal direction of the endoluminal device.

Preferably, that the at least one composite yarn and/or the at least one further polymer yarn, preferably the at least one composite yarn and the at least one further polymer yarn, extend in unidirectional spirals, in particular unidirectional helices, along a longitudinal direction of the endoluminal device.

More preferably, the at least one composite yarn and/or the at least one further polymer yarn, preferably the at least one composite yarn and the at least one further polymer yarn, extend in oppositely directed spirals, in particular oppositely directed helices, along a longitudinal direction of the endoluminal device.

The spirals, in particular helices, in particular as mentioned in the three preceding paragraphs, may have an increase from 0.01 mm to 20 mm, in particular 0.1 mm to 15 mm, preferably 0.3 mm to 10 mm. The increase as disclosed in this paragraph is especially advantageous in terms of an increased radial stability and in terms of increased material per surface of the endoluminal device.

Preferably, the spirals, in particular helices, are connected to each other, in particular at crossing points (points of intersection) of the spirals, in particular helices. Thus, the radial stiffness of the endoluminal device can be advantageously increased. The spirals, in particular helices, may be connected to each other by means of material bonding engagement and/or by means of a textile technique, in particular at crossing points (points of intersection) of the spirals, in particular helices. The material bonding engagement may be selected from the group consisting of gluing, welding such as laser welding and/or electron beam welding, melting and a combination of at least two of said material bonding engagements. The textile technique may be selected from the group consisting of weaving, knitting, braiding and a combination of at least two of said textile techniques.

In a further embodiment, the endoluminal device comprises a plurality of enlacements (loops), which are preferably arranged in a circumferential direction of the endoluminal device or which preferably surround the endoluminal device along its circumference. The enlacements (loops) may be connected to the spirals, in particular helices, as mentioned in the previous paragraphs. For example, the enlacements (loops) may be connected to the spirals, in particular helices, by means of a textile technique such as weaving, knitting or braiding or by means of a material bonding engagement such gluing, welding or melting. Preferably, each enlacement (loop) is embodied as a composite yarn. The composite yarn preferably comprises at least one polymer yarn, i.e. one polymer yarn or a plurality of polymer yarns, and at least one alloy wire, i.e. one alloy wire or a plurality of alloy wires. Further, the composite yarn is preferably a covered yarn, in particular a wrapped yarn. As regards further features and advantages of the composite yarn, reference is made in its entirety to the embodiments regarding the at least one composite yarn disclosed in the previous description which do apply accordingly. In particular, the at least one polymer yarn of the composite yarn in the context of the enlacements (loops) may comprise or consist of the same polymer as the at least one polymer yarn of the at least one composite yarn disclosed in the previous description. Further, the at least one alloy wire of the composite yarn in the context of the enlacements (loops) may comprise or consist of the same alloy as the at least one alloy wire of the at least one composite yarn disclosed in the previous description. Preferably, the at least one polymer yarn of the composite yarn in the context of the enlacements may comprise or consist of polylactide, in particular poly(L-lactide), and the at least one alloy wire of the composite yarn in the context of the enlacements may comprise or consist of a magnesium alloy.

In a further embodiment, the endoluminal device comprises additional composite yarns, in particular in the form of enlacements (loops). The additional composite yarns are preferably arranged in a circumferential direction of the spirals, in particular helices, as mentioned in the previous paragraphs or preferably surround the spirals, in particular helices, as mentioned in the previous paragraphs. Thus, the radial stiffness and/or suspension of the endoluminal device can be considerably increased. The additional composite yarns may be equally or differently embodied as the at least one composite yarn described in the previous description. Preferably, the additional composite yarns are equally embodied as the at least one composite yarn described in the previous description. With respect to further features and advantages of the additional composite yarns, reference is made to the features and advantages of the at least one composite described in the previous description which do apply accordingly with respect to the additional composite yarns.

In a further embodiment, the endoluminal device comprises a plurality of composite yarns, wherein a number of the composite yarns, i.e. one composite yarns or several composite yarns, extend in at least one spiral, i.e. in one spiral or in a plurality of spirals, preferably in at least one helix, i.e. in one helix or in a plurality of helices, along a longitudinal direction of the endoluminal device and a remaining number of the composite yarns, i.e. one composite yarn or several composite yarns, is arranged in a circumferential direction of the endoluminal device, in particular of the at least one spiral, preferably of the at least one helix, or surrounds the endoluminal device, in particular the at least one spiral, preferably the at least one helix, along its circumference. By means of the composite yarns being arranged in the circumferential direction of the endoluminal device or surrounding the endoluminal device along its circumference, the radial stiffness and/or suspension of the endoluminal device can be significantly increased. The composite yarns may be equally or differently embodied. Preferably, the remaining number of the composite yarns is embodied as an enlacement (loop) or as enlacements (loops). The at least one spiral, in particular the at least one helix, may be embodied as at least one unidirectional spiral, in particular at least one unidirectional helix, or as oppositely directed spirals, in particular oppositely directed helices. With respect to further features and advantages, in particular in terms of the composite yarns, reference is made in its entirety to the previous description.

Further, the at least one composite yarn, in particular the at least one alloy wire thereof and/or the at least one polymer yarn thereof, and/or the at least one further polymer yarn and/or the additional composite yarns and/or the enlacements, may be covered, in particular (only) partially covered or completely covered, by a coating. The coating may be a non-textile or textile coating. Preferably, the coating is embodied as a non-textile coating.

The coating may be advantageously adapted to increase the radial stability of the endoluminal device.

Preferably, the coating comprises or consists of a polymer, in particular a polymer which is adapted to facilitate a mutual connection of the at least one composite yarn and the at least one further polymer yarn, in particular by material bonding engagement such as gluing, welding or melting.

Preferably, the polymer of the coating is selected from the group consisting of polylactide, polyglycolide, poly(3-hydroxybutyrate), poly(4-hydroxybutyrate), polycaprolactone, poly(trimethylene carbonate) and a blend of at least two of said polymers.

The polylactide is preferably selected from the group consisting of poly(L-lactide), poly(D,L-lactide), poly(D-lactide) and a blend of at least two of said polymers. More preferably, the polylactide is poly(L-lactide).

Further, the polymer may be a copolymer. Preferably, the copolymer comprises or consists of repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units.

More preferably, the copolymer is selected from the group consisting of poly(L-lactide-co-glycolide), poly(D,L-lactide-co-glycolide), poly(D-lactide-co-glycolide), poly(L-lactide-co-caprolactone), poly(D,L-lactide-co-caprolactone), poly(D-lactide-co-caprolactone), poly(3-hydroxybutyrate-co-3-hydroxyvalerate), poly(3-hydroxybutyrate-co-4-hydroxybutyrate), poly(3-hydroxybutyrate-co-3-hydroxyoctanoate) and a blend of at least two of said copolymers.

It goes without saying that the polymer of the coating may further be any blend of at least two of the above-mentioned polymers and copolymers, respectively.

The coating may further comprise a degradation-retarding agent such as rubidium or compounds thereof. Thus, if the at least one alloy wire of the at least one composite yarn and/or of the composite yarn in the context of the enlacements comprise or consist of a biodegradable alloy, degradation of the at least one wire can be adjusted in a timely manner.

The coating may further comprise at least one agent, in particular at least one anti-proliferative agent, and optionally an excipient as detailed in the following.

The endoluminal device may comprise at least one agent, i.e. one agent or a plurality of agents, and optionally at least one excipient, i.e. one excipient or a plurality of excipients. In particular, the endoluminal device may comprise a coating comprising at least one agent and optionally at least one excipient. For example, the polymer yarns and/or the at least one alloy wire may comprise at least one agent and optionally at least one excipient or a respective coating.

The at least one agent is preferably selected from the group consisting of anti-proliferative agent, antimicrobial, in particular antibiotic agent, wound healing-promoting agent, disinfecting agent, anti-inflammatory agent, growth factor, cell-differentiating factor, cell-adhesive factor, cell-recruiting factor, cell receptor, cell-binding factor, cytokine, peptide, structural protein, extracellular protein such as collagen, serum protein such as albumin, polysaccharide such as hyaluronic acid, oligonucleotide, polynucleotide, DNA, RNA, radio-opaque agent, a salt of at least two of said agents, a stereoisomer, more particular a diastereomer, of at least two of said agents and a mixture of at least two of said agents.

The at least one agent is preferably an anti-proliferative agent or a mixture of anti-proliferative agents.

The anti-proliferative agent is in particular selected from the group consisting of limus derivatives, sirolimus, everolimus, biolimus A9, tacrolimus, zotarolimus, paclitaxel, docetaxel, methotrexate, azathioprine, vincristine, vinblastine, fluorouracil, doxorubicin hydrochloride, mitomycin and a mixture of at least two of said anti-proliferative agents.

The at least one excipient may be selected from the group consisting of probucol, polyvinyl pyrrolidone, glycerine, polyhydroxyethyl, methacrylates, polyethylene glycole, polypropylene glycole, butylated hydroxytoluene (BHT), resveratol, polyvinyl alcohol, polydioxanone, polycaprolactone, polygluconate, poly(lactic acid)polyethylene oxide copolymer, modified cellulose, polyhydroxybutyrate, polyamino acids, polyphosphate esters, polyvalerolactones, poly-e-decalactones, polylactonic acid, polyglycolic acid polylactides, polyglycolides, copolymers of the polylactides and polyglycolides, poly-e caprolactone, polyhydroxybutyric acid, polyhydroxybutyrates, polyhydroxyvalerates, polyhydroxybutyrate-co-valerates, poly(1,4-dioxane-2,3-dione), poly(1,3-dioxane-2-one), poly-para-dioxanones, polyanhydrides, polymaleic acid anhydrides, polyhydroxy methacrylates, fibrin, polycyanoacrylates, polycaprolactone dimethylacrylates, poly-b-maleic acid polycaprolactone butyl acrylates, multiblock polymers from oligocaprolactonediols and oligodioxanonediols, polyether ester multiblock polymers from PEG and polybutylene terephthalate, polypivotolactones, polyglycolic acid trimethyl carbonates, polycaprolactone, glycolides, poly(g-ethyl glutamate), poly (DTH-iminocarbonate), poly(DTE-co-DT-carbonate), poly (bisphenol A-iminocarbonate), polyorthoesters, polyglycolic acid trimethyl carbonates, polytrimethyl carbonates polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, waxes, oils, polyunsaturated fatty acids, eicosapentaenoic acid, timnodonic acid, docosahexaenoic acid, arachidonic acid, linoleic acid, alpha-linolenic acid, gamma-linolenic acid, carrageenans, fibrinogen, agar-agar, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and its derivatives, heparan sulfates and its derivates, heparins, chondroitin sulfate, dextran, beta-cyclodextrins, copolymers with PEG and polypropylene glycol, gum arabic, guar, gelatin, collagen, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, polyisobutylenes, fluorosilicones, carboxymethyl chitosans, polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, EPDM gums, silicones such as polysiloxanes, polydimethylsiloxanes, polyvinyl halogens, cellulose ethers, cellulose triacetates, shellac, poly-para-xylylenes and a mixture of at least two of said excipients.

Further, at least one end, in particular ends, preferably a distal end and a proximal end, of the endoluminal device may be formed stiffened, in particular by means of a solvent treatment. For a suitable solvent treatment, solvents, in particular organic solvents such as chloroform, dichloromethane, trichloromethane, acetone, tetrahydrofuran, ethanol or a mixture of at least two of said solvents can be used. Thus, it can be advantageously avoided that the ends of the endoluminal device, in particular yarn ends thereof, fan out.

Further, the endoluminal device may be formed as a textile, in particular woven, knitted or braided, device. More preferably, the endoluminal device is embodied as a braided device.

Further, the endoluminal device may be a tubular device, in particular a tubular and textile, in particular woven, knitted or braided, device. More preferably, the endoluminal device is embodied as a tubular braided device.

Further, the endoluminal device may be a bifurcated endoluminal device.

Further, the endoluminal device may be a thermoset (heat fixed or thermo-fixed) device.

The term "thermoset device" as used according to the present invention refers to an endoluminal device which has been manufactured onto a mandrel, in particular by means of a textile technique such as weaving, knitting or braiding, and which together with the mandrel has been subsequently heated, in particular applying a temperature from 35° C. to 150° C., during a defined time, in particular during a time period of 1 minute to 1 day, in order to give the endoluminal device dimensional and shape stability.

Further, the endoluminal device may be adapted to effect a blood wall coverage, in particular a venous wall coverage or an arterial wall coverage, preferably an arterial wall coverage, in the range of 5% to 60%, in particular 10% to 50%, preferably 12% to 40%.

Further, the endoluminal device may exhibit a diameter from 1.0 mm to 10 mm, in particular 1.5 mm to 8.0 mm, preferably 2.0 mm to 6.0 mm.

Further, the endoluminal device may be a ready-for-use endoluminal device. For example, the length of the endoluminal device can be tailored by means of laser cutting.

In a further embodiment, the endoluminal device is an endovascular, in particular endovenous or endoarterial, more preferably an endoarterial, device.

More preferably, the device according to the present invention is a stent, in particular an endovascular stent, in particular an endovenous or endoarterial stent, more preferably an endoarterial stent. The stent may in particular be a self-expandable stent or a balloon-expandable stent.

It goes without saying that the endoluminal device according to the first aspect of the invention may be the result of any combination of the preceding disclosed embodiments.

A second aspect of the invention relates to a method for manufacturing an endoluminal device, in particular an endoluminal device according to the first aspect of the invention.

The method comprises the step of:
depositing at least one composite yarn onto a mandrel, wherein the composite yarn comprises at least one polymer yarn and at least one alloy wire, wherein the at least one polymer yarn comprises or consists of a polymer, in particular a biodegradable polymer, selected from the group consisting of polylactide, polyglycolide, poly(3-hydroxybutyrate), poly(4-hydroxybutyrate), polycaprolactone, poly(trimethylene carbonate), copolymer comprising or consisting of repeating monomer units selected from the group consisting of lactide units, glycolide units, 6-hydroxyhexanoic acid units, 3-hydroxybutyrate units, 4-hydroxybutyrate units, trimethylene carbonate units and a combination of at least two of said monomer units, and a blend of at least two of said polymers, and the at least one alloy wire comprises or consists of an alloy, in particular a biocompatible alloy, selected from the group consisting of magnesium alloy, zinc alloy, iron alloy, alloyed stainless steel, cobalt-chromium alloy and a combination of at least two of said alloys.

In an embodiment, the method further comprises the step of
depositing at least one further polymer yarn onto the mandrel.

Preferably, the at least one composite yarn and/or the at least one further polymer yarn are deposited onto the mandrel by means of a textile technique, in particular by means of weaving, knitting or braiding, preferably by braiding.

Further, it is preferred that the at least one composite yarn and/or the at least one further polymer yarn are deposited onto the mandrel in spirals, in particular helices, along a longitudinal direction of the mandrel.

More preferably, the at least one composite yarn and/or the at least one further polymer yarn, in particular the at least one composite yarn and the at least one further polymer yarn, are deposited onto the mandrel in unidirectional spirals, in particular unidirectional helices, along a longitudinal direction of the mandrel.

Especially preferably, the at least one composite yarn and/or the at least one further polymer yarn, in particular the at least one composite yarn and the at least one further polymer yarn, are deposited onto the mandrel in oppositely directed spirals, in particular oppositely directed helices, along a longitudinal direction of the mandrel.

The at least one composite yarn and/or the at least one further polymer yarn may be connected to each other, preferably at crossing points (points of intersection) of the spirals, in particular helices, as mentioned in the preceding paragraphs. For example, the at least one composite yarn and/or the at least one further polymer yarn may be connected to each other by means of a textile technique such as weaving, knitting or braiding. Preferably, the at least one composite yarn and/or the at least one further polymer yarn are connected to each other by means of braiding. Alternatively, the at least one composite yarn and/or the at least one further polymer yarn may be connected to each other by material bonding engagement, such as by gluing, welding or melting.

The method may further comprise the step of
arranging enlacements (loops), in particular equidistant to each other, in a circumferential direction of the mandrel.

The enlacements (loops) may be connected to the at least one composite yarn and/or the at least one further polymer yarn, in particular to the at least one composite yarn and the at least one further polymer yarn, by means of a textile technique such as weaving, knitting or braiding or by means of a material bonding engagement such as gluing, welding or melting.

Preferably, each enlacement (loop) is embodied as composite yarn, preferably as composite yarn comprising at least one polymer yarn and at least one alloy wire. Preferably, the at least one polymer yarn comprises or consists of the same polymer than the at least one polymer yarn of the at least one composite yarn as described in the preceding paragraphs. Further, preferably the at least one alloy wire comprises or consists of the same alloy as the at least one alloy wire of the at least one composite yarn as described in the preceding paragraphs.

The method may further comprise the step of
thermosetting the endoluminal device.

Preferably, the step of thermosetting is performed at a temperature from 35° C. to 150° C. Further, the step of thermosetting may be performed during a time period of 1 minute to 1 day.

The method may further comprise the step of
subjecting the endoluminal device, in particular at least one end, in particular ends (e.g. a distal end and a proximal end), thereof to a solvent treatment.

Thus, fanning out of ends, in particular yarn ends, can be advantageously circumvented. Preferably, an organic solvent such as chloroform, dichloromethane, trichloromethane, acetone, tetrahydrofuran, ethanol or a mixture of at least two of said solvents is used for the solvent treatment.

The method may further comprise the step of
equipping the endoluminal device with at least one agent, preferably at least one anti-proliferative agent, and optionally at least one excipient.

The method may further comprise the step of
tailoring, in particular cutting, the endoluminal device.

With respect to further features and advantages of the method, reference is made in its entirety to the description of the endoluminal device according to the first invention aspect. The features and advantages described in terms of the endoluminal device according to the first invention aspect, in particular in terms of the at least one composite yarn and/or the at least one polymer yarn and/or the at least one alloy wire and/or the at least one further polymer yarn and/or the enlacements, do apply accordingly with respect to the method for manufacturing an endoluminal device according to the second invention aspect.

According to a third aspect, the invention relates to a surgical system or kit, preferably for the treatment of stenosis and/or for preventing restenosis disorders.

The system and kit, respectively, comprises an endoluminal device according to the first aspect of the invention.

Additionally, the system and kit, respectively, comprises a delivery instrument, in particular a delivery catheter, preferably a balloon catheter.

The delivery instrument is preferably adapted to deliver the endoluminal device within a body lumen of a body vessel, in particular of a venous or arterial, preferably arterial, blood vessel.

The endoluminal device is preferably attached to the delivery device, in particular crimped onto the delivery device.

Preferably, the endoluminal device is a stent.

With respect to further features and advantages of the system and kit, respectively, in particular with respect to the endoluminal device, reference is made to the embodiments described under the first aspect of the invention. It goes without saying that the features and advantages described in terms of the endoluminal device during the first aspect of the invention do apply accordingly with respect to the system and kit, respectively of the third aspect of the invention.

According to a fourth aspect, the invention relates to a further endoluminal device, preferably for the treatment of stenosis and/or for preventing restenosis disorders. Thus, also the endoluminal device of the fourth invention aspect is preferably a stent.

The endoluminal device comprises a plurality of polymer yarns and at least one alloy wire, i.e. one alloy wire or a plurality of alloy wires.

The polymer yarns comprise or consist of a polymer, in particular a biodegradable polymer.

Preferably, the polymer exhibits a slower biodegradation rate than the alloy of the at least one alloy wire. Thus, the alloy of the at least one alloy wire preferably increases the endoluminal device's mechanical stability during an initial and medium-term stage, in particular during storage (e.g. when crimped onto a delivery catheter) during implantation and in particular during a couple of months after implantation, while the polymer of the polymer yarns advantageously facilitates a long-term support of the treated body lumen portion, and thus is advantageously responsible for a long-term patency rate. Preferably, the polymer of the polymer yarns has a biodegradation rate of 1 to 3 years.

The polymer is preferably selected from the group consisting of polylactide, polyglycolide, poly(3-hydroxybutyrate), poly(4-hydroxybutyrate), polycaprolactone, poly(trimethylene carbonate) and a blend, i.e. a mixture, of at least two of said polymers.

Further, the polymer is preferably a copolymer. More preferably, the copolymer comprises or consists of repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units.

Further, the polymer may be any combination of at least two of the afore-mentioned polymers and copolymers, respectively.

The at least one alloy wire comprises or consists of an alloy, typically a biocompatible alloy.

Further, the alloy may be a biodegradable, a partially biodegradable or a non-biodegradable alloy. Preferably, the alloy of the at least one alloy wire is a biodegradable alloy. More preferably, the alloy of the at least one alloy wire exhibits a faster biodegradation rate than the polymer of polymer yarns. Due to a preferably permanent biodegradation of the alloy, a continuously increasing organ apposition, in particular blood vessel apposition, preferably artery apposition, can be accomplished due to an increasing expansion of the polymer of the polymer yarns into the wall containing the bodily lumen. In particular, the alloy of the at least one alloy wire may have a biodegradation rate of 1 to 4 months.

Preferably, the alloy is selected from the group consisting of magnesium alloy, zinc alloy, iron alloy, cobalt-chromium alloy and a combination of at least two of said alloys. In particular, the iron alloy may be an alloyed stainless steel.

In a preferred embodiment, the polymer yarns comprise or consist of polylactide and the at least one alloy wire preferably comprises or consists of an alloy selected from the group consisting of magnesium alloy, zinc alloy, iron alloy, cobalt-chromium alloy and a combination of at least two of said alloys.

More preferably, the polylactide is selected from the group consisting of poly(L-lactide), poly(D,L-lactide), poly(D-lactide) and a blend of at least two of said polymers.

More preferably, the polylactide is poly(L-lactide).

Further, the polymer yarns may comprise or consist of polyglycolide and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of poly(3-hydroxybutyrate) and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of poly(4-hydroxybutyrate) and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of polycaprolactone and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of poly(trimethylene carbonate) and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of a copolymer and the at least one alloy wire may comprise or consist of an alloy selected from the group consisting of magnesium alloy, zinc alloy, iron alloy, cobalt-chromium alloy and a combination of at least two of said alloys.

Preferably, the copolymer comprises or consists of repeating lactide units. The lactide units may be L-lactide units and/or D-lactide units. Preferably, the lactide units are L-lactide units.

More preferably, the copolymer is selected from the group consisting of poly(L-lactide-co-glycolide), poly(D,L-lactide-co-glycolide), poly(D-lactide-co-glycolide), poly(L-lactide-co-caprolactone), poly(D,L-lactide-co-caprolactone), poly(D-lactide-co-caprolactone), poly(3-hydroxybutyrate-co-3-hydroxyvalerate), poly(3-hydroxybutyrate-co-4-hydroxybutyrate), poly(3-hydroxybutyrate-co-3-hydroxyoctanoate) and a blend of at least two of said copolymers.

Further, the polymer yarns may comprise or consist of a copolymer comprising or consisting of repeating glycolide units and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of a copolymer comprising or consisting of repeating 6-hydroxyhexanoic acid units and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of a copolymer comprising or consisting of repeating 3-hydroxybutyrate units and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of a copolymer comprising or consisting of repeating 4-hydroxybutyrate units and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of a copolymer comprising or consisting of repeating trimethylencarbonate units and the at least one alloy wire may comprise or consist of an alloy selected from the group consisting of magnesium alloy, zinc alloy, iron alloy, cobalt-chromium alloy and a combination of at least two of said alloys.

Further, the polymer yarns may comprise or consist of any blend of at least two polymers and copolymers, respectively as mentioned in the preceding embodiments.

Preferably, the polymer yarns comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire preferably comprises or consists of a magnesium alloy.

The term "magnesium alloy" as used according to the present invention preferably defines a mixture of magnesium, typically as the main constituent, with at least one further metal. The at least one further metal may be selected from the group consisting of aluminium, bismuth, titan, wolfram, cadmium, palladium, rare earth element, gadolinium, dysprosium, neodymium, europium, yttrium, iron, thorium, calcium, strontium, zirconium, lithium, rubidium, manganese, nickel, lead, silver, cobalt, chromium, silicon, tin, calcium, antimony, copper, zinc and an alloy of at least two of said metals.

More preferably, the term "magnesium alloy" as used according to the present invention defines an alloy which along magnesium, in particular as the main constituent, comprises at least one further metal which is selected from the group consisting of calcium, zirconium, yttrium, dysprosium, neodymium, europium and a combination of at least two of said metals.

In particular, the magnesium alloy may contain the following components based on the total weight of the alloy:
  5.0% by weight to 25.5% by weight dysprosium
  0.01% by weight to 5.0% by weight neodymium and/or europium
  0.1% by weight to 3.0% by weight zinc
  0.1% by weight to 2.0% by weight zirconium
  balance to 100% by weight magnesium.

Further, the magnesium alloy may be selected from the group consisting of magnesium alloy comprising (—along magnesium —) yttrium, neodymium, zinc and zirconium, magnesium alloy comprising (—along magnesium —) yttrium, europium, zinc and zirconium, magnesium alloy comprising (—along magnesium —) dysprosium, neodymium, zinc and zirconium, magnesium alloy comprising (—along magnesium-) dysprosium, europium, zinc and zirconium, magnesium alloy comprising (—along magnesium —) calcium, neodymium, zinc and zirconium, magnesium alloy comprising (—along magnesium —) calcium, europium, zinc and zirconium and a combination of at least two of said alloys.

Further, the magnesium alloy may be an alloy which is commercially available under the abbreviation "AZ31b". This magnesium alloy contains 2.5 percent by weight to 3.5 percent by weight of aluminium, at most 0.2 percent by weight of manganese, 0.6 percent by weight to 1.4 percent by weight of zinc, at most 0.005 percent by weight of iron, at most 0.05 percent by weight of copper, at most 0.10 percent by weight of silicon, at most 0.04 percent by weight of calcium and at most 0.005 percent by weight of nickel, each in relation to the total weight of the magnesium alloy.

Further, the magnesium alloy may be an alloy which is commercially available under the abbreviation "WE43". This magnesium alloy contains 3.7 to 4.3 percent by weight of yttrium, 2.4 to 4.4 percent by weight of rare earths and 0.4 percent by weight of zirconium, each in relation to the total weight of the magnesium alloy.

Further, the polymer yarns may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of a zinc alloy.

The term "zinc alloy" as used according to the present invention preferably defines a mixture of zinc, typically as the main constituent, with at least one further metal. The at least one further metal may be selected from the group consisting of magnesium, aluminium, bismuth, titan, wolfram, cadmium, palladium, rare earth element, gadolinium, dysprosium, neodymium, europium, yttrium, iron, thorium, calcium, strontium, zirconium, lithium, rubidium, manganese, nickel, lead, silver, cobalt, chromium, silicon, tin, calcium, antimony, copper and an alloy of at least two of said metals.

More preferably, the term "zinc alloy" as used according to the present invention defines an alloy which along zinc, in particular as the main constituent, comprises at least one further metal which is selected from the group consisting of iron, lithium, calcium, magnesium, a rare earth element (such as gadolinium and/or dysprosium and/or neodymium and/or europium and/or yttrium) and a combination of at least two of said metals.

In particular, the zinc alloy may be selected from the group consisting of zinc alloy comprising (—along zinc —) iron and lithium, zinc alloy comprising (—along zinc —) iron and calcium, zinc alloy comprising (—along zinc —) iron and magnesium and a combination of at least two of said alloys.

Further, the polymer yarns may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of an iron alloy.

The term "iron alloy" as used according to the present invention preferably defines a mixture of iron, typically as the main constituent, with at least one further metal. The at least one further metal may be selected from the group consisting of magnesium, aluminium, bismuth, titan, wolfram, cadmium, palladium, rare earth element, gadolinium, dysprosium, neodymium, europium, yttrium, thorium, calcium, strontium, zirconium, lithium, rubidium, manganese, nickel, lead, silver, cobalt, chromium, silicon, tin, calcium, antimony, copper, zinc and an alloy of at least two of said metals.

More preferably, the term "iron alloy" as used according to the present invention defines an alloy which along iron, in particular as the main constituent, comprises at least one further metal which is selected from the group consisting of manganese, palladium, silicon and a combination of at least two of said metals. In particular, the iron alloy may—along iron—comprise manganese and/or palladium and/or silicon.

Further, the iron alloy as used according to the present invention may be an alloyed stainless steel. Preferably, the alloyed stainless steel comprises along iron, in particular as the main constituent, at least one further metal selected from the group consisting of chromium, nickel, platinum, molybdenum and a combination of at least two of said alloys. In particular, the alloyed stainless steel may—along iron—comprise chromium and nickel and/or platinum and molybdenum, in particular chromium and nickel or platinum and molybdenum. For example, the alloyed stainless steel may be a steel of type AISI 316 L.

Accordingly, the polymer yarns may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of an alloyed stainless steel.

Further, the polymer yarns may comprise or consist of a polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers and the at least one alloy wire may comprise or consist of a cobalt-chromium alloy.

The term "cobalt-chromium alloy" as used according to the present invention preferably defines a mixture of at least cobalt and chromium, and optionally with at least one further metal. The optional at least one further metal may be selected from the group consisting of magnesium, aluminium, bismuth, titan, wolfram, cadmium, rare earths, gadolinium, dysprosium, neodymium, europium, yttrium, iron, thorium, calcium, strontium, zirconium, lithium, rubidium, manganese, nickel, lead, silver, silicon, tin, calcium, antimony, copper, zinc and an alloy of at least two of said metals.

More preferably, the term "cobalt-chromium alloy" as used according to the present invention defines an alloy which along cobalt and chromium, in particular as the main constituents, comprises at least one further metal which is selected from the group consisting of nickel, tungsten (wolfram) and a combination of at least two of said metals. For example, the cobalt-chromium alloy may be a cobalt-chromium alloy according to ASTM F90 or ISO 5832-5.

Further, the at least one alloy wire may comprise or consist of any combination of at least two alloys as mentioned in the preceding embodiments.

In an especially preferred embodiment, the polymer yarns comprise or consist of polylactide, in particular poly(L-lactide), and the at least one alloy wire comprises or consists of a magnesium alloy. With respect to further details, in particular in terms of polylactide and magnesium alloy, reference is made in its entirety to previous description. The features and advantages disclosed therein apply accordingly.

Further, the polymer yarns may comprise or consist of a copolymer comprising or consisting of repeating lactide units, in particular repeating L-lactide units, and the at least one alloy wire may comprise or consist of a magnesium alloy. With respect to further details, in particular in terms of the copolymer and magnesium alloy, reference is made in its entirety to previous description. The features and advantages disclosed therein apply accordingly.

Further, the polymer yarns may have a rounded, in particular circular or oval, cross-section.

Alternatively, the polymer yarns may have a non-circular cross-section such as a trigonal, square, quadrangular, trapezoidal, rhombic, pentagonal, hexagonal or star-like cross-section.

A circular or triangular cross-section of the polymer yarns is especially advantageous, since both types of cross-sections allow for a better embedding of the endoluminal device, in a wall surrounding a body lumen, and thus facilitate a secure and in particular long-term positioning of the device within a bodily lumen.

Further, the polymer yarns may exhibit a diameter from 5 µm to 300 µm, in particular 10 µm to 200 µm, preferably 15 µm to 150 µm Further, the polymer yarns may exhibit a linear density from >0.01 tex [g/km] to 150 tex [g/km]tex in particular 0.09 tex [g/km] to 100 tex [g/km], preferably 0.2 tex [g/km] to 75 tex [g/km].

Further, the polymer yarns may exhibit a length from 5 mm to 9000 mm, in particular 8 mm to 7000 mm, preferably 10 mm to 5000 mm.

Further, the polymer yarns may be differently embodied polymer yarns, preferably in terms of length, cross-section, diameter, linear density, biodegradation rate, polymer, number of fibres and combinations thereof.

Further, the polymer yarns may comprise or consist of (only) one polymer fibre. In other words, each polymer yarn may be embodied as (only) one polymer fibre.

Further, the polymer yarns may comprise or consist of a plurality of polymer fibres, in particular differently embodied polymer fibres, preferably in terms of length, cross-section, diameter, linear density, biodegradation rate, polymer and combinations thereof.

The polymer yarns may in particular comprise or consist of 1 to 50, in particular 2 to 30, preferably 3 to 20, polymer fibres.

Further, the polymer fibres may exhibit a diameter from 0.5 μm to 300 μm, in particular 2 μm to 200 μm, preferably 5 μm to 150 μm.

Further, the polymer fibres may exhibit a linear density from less than 0.01 tex [g/km] to 150 tex [g/km], in particular 0.09 tex [g/km] to 100 tex [g/km], preferably 0.2 tex [g/km] to 75 tex [g/km].

Further, the polymer fibres may exhibit a length from 5 mm to 9000 mm, in particular 8 mm to 7000 mm, preferably 10 mm to 5000 mm.

Further, the polymer fibres may have a round, in particular circular or oval, cross-section.

Alternatively, the polymer fibres may have a non-circular cross-section, such as a trigonal, square, quadrangular, trapezoidal, rhombic, pentagonal, hexagonal or stark-like cross-section.

Advantageously, the stiffness and strength, and thus in particular a long-term patency rate of the endoluminal device, can be purposefully controlled by the polymer yarns' parameters and or by the respective parameters of the polymer yarns' fibre(s) as described in the preceding embodiments.

Further, the polymer yarns may comprise a biodegradation-retarding agent, in particular rubidium or a rubidium compound such as a rubidium alloy. Thus, in case of a biodegradable alloy for the at least one alloy wire, biodegradation rate of the at least one alloy wire can be purposefully influenced.

Further, the at least one alloy wire may have a round, in particular circular or oval, cross-section.

Alternatively, the at least one alloy wire may have a non-circular cross-section, in particular a trigonal, square, quadrangular, trapezoidal, rhombic, pentagonal, hexagonal or star-like cross-section.

A circular or triangular cross-section of the at least one alloy wire is especially advantageous, since both types of cross-sections allow for a better embedding of the endoluminal device, in a wall surrounding a body lumen, and thus facilitate a secure and in particular long-term positioning of the device within a bodily lumen.

Further, the at least one alloy wire may exhibit a diameter from 1 μm to 300 μm, in particular 5 μm to 200 μm, preferably 10 μm to 150 μm. Thus, in particular time-dependent mechanical characteristics in case of a biodegradable alloy, such as radial strength and/or fracture toughness, can be purposefully controlled.

Further, the at least one alloy wire may exhibit a length from 5 mm to 9000 mm, in particular 8 mm to 7000 mm, preferably 10 mm to 5000 mm.

Further, the at least one alloy wire may have a grain size from more than 12 to 3, in particular more than 12 to 6, preferably more than 12 to 8, according to ASTM 112-12. The grain size disclosed in this paragraph advantageously allows deformation of the at least one alloy wire without destruction. Alternatively, the at least one alloy wire may be made of a monolithic grain size.

Further, the at least one wire may have a core-sheath structure. In other words, the at least one wire may comprise a core and a sheath, wherein the sheath at least partially, in particular only partially, or completely surrounds or covers the core. Principally, the core and/or sheath may comprise or consist of an alloy or a combination of at least two alloys as disclosed in the previous description. Thus, preferably, the core and/or sheath may comprise or consist of an alloy selected from the group consisting of magnesium alloy, zinc alloy, iron alloy, alloyed stainless steel, cobalt-chromium alloy and combinations of at least two of said alloys. Preferably, the core comprises or consists of a biodegradable alloy and the sheath comprises or consists of non-biodegradable alloy or slower biodegradable alloy, i.e. an alloy which exhibits a slower biodegradation rate than the alloy of the core. For example, the core may comprise or consist of a magnesium alloy, while the sheath may comprise or consist of a zinc alloy. Alternatively, the core may comprise or consist of a biodegradable alloy such as a magnesium alloy, while the sheath may comprise or consist of a non-biodegradable elementary metal such as titan or wolfram or compounds thereof. Thus, biodegradation of the core may be advantageously controlled, in particular retarded, and/or biocompatibility of the endoluminal device can be adjusted.

Further, the at least one alloy wire may be embodied as one alloy wire. In other words, the at least one alloy wire may be (only) one alloy wire. It goes without saying that the features and advantages disclosed in the previous description in respect of the at least one alloy wire do apply accordingly, if the at least one alloy wire is embodied as (only) one alloy wire.

Further, the at least one alloy wire may correspond to a plurality of alloy wires, preferably to a plurality of differently embodied alloy wires. In other words, the at least one alloy wire may be defined as a plurality of alloy wires. Preferably, the alloy wires are differently embodied in terms of length, cross-section, diameter, biodegradation rate, structure, alloy or combinations thereof. It goes without saying that the features and advantages disclosed in the previous description in respect of the at least one alloy wire do apply accordingly, in particular to each alloy wire or only a part of the alloy wires, if the at least one alloy wire is embodied as a plurality of alloy wires. Thus, as regards length, diameter, cross-section, biodegradation rate, structure and alloy, reference is made in its entirety to the previous description.

In case of a biodegradable alloy, under stability aspects a plurality of alloy wires has the advantage that a progressive biodegradation of one alloy wire may be compensated by at least one further alloy wire, in particular by several further alloy wires.

For example, the at least one alloy wire may comprise or consist of 1 to 40, in particular 2 to 30, preferably 3 to 20, alloy wires.

Further, the at least one alloy wire may comprise or consist of at least two alloy wires which are differently embodied in terms of diameter. For example, the at least one alloy wire may comprise a first alloy wire having a diameter of 30 μm and a second alloy wire having a diameter of 50 μm.

Further, the at least one alloy wire may comprise at least two alloy wires which are differently embodied in terms of the alloy. For example, the at least one alloy wire may comprise a first alloy wire comprising or consisting of a biodegradable alloy and a second alloy wire comprising or consisting of a non-biodegradable or a slower biodegradable alloy, i.e. an alloy which exhibits a slower biodegradation rate than the alloy of the first alloy wire. Preferably, the biodegradable alloy is a magnesium alloy. The non-biodegradable or slower biodegradable alloy is preferably a zinc alloy. With respect to further features and advantages of the magnesium alloy and/or zinc alloy, reference is made in its entirety to the previous description.

In a further embodiment, the polymer yarns and/or the at least one alloy wire, in particular the polymer yarns and the at least one alloy wire, are connected to each other, in particular by means of a textile technique and/or by means of a material bonding engagement. The textile technique may be selected from the group consisting of weaving, knitting, braiding and a combination of at least two of said textile techniques. The material bonding engagement may be selected from the group consisting of gluing, welding (such as laser welding and/or electron beam welding), melting and a combination of at least two of said material bonding engagements.

In a further embodiment, the polymer yarns and/or the at least one alloy wire, preferably the polymer yarns and the at least one alloy wire, extend in spirals, in particular helices, along a longitudinal direction of the endoluminal device.

Preferably, the polymer yarns and/or the at least one alloy wire, preferably the polymer yarns and the at least one alloy wire, extend in unidirectional spirals, in particular unidirectional helices, along a longitudinal direction of the endoluminal device.

More preferably, the polymer yarns and/or the at least one alloy wire, preferably the polymer yarns and the at least one alloy wire, extend in oppositely directed spirals, in particular oppositely directed helices, along a longitudinal direction of the endoluminal device.

The spirals, in particular helices, in particular as mentioned in the three preceding paragraphs, may have an increase from 0.01 mm to 20 mm, in particular 0.1 mm to 15 mm, preferably 0.3 mm to 10 mm. The increase as disclosed in this paragraph is especially advantageous in terms of an increased radial stability and in terms of increased material per surface of the endoluminal device.

Further, the spirals, in particular helices, are preferably connected to each other, in particular at crossing points (points of intersection) of the spirals, in particular helices. Thus, the radial stiffness of the endoluminal device can be advantageously increased. The spirals, in particular helices, may be connected to each other by means of material bonding engagement and/or by means of a textile technique, in particular at crossing points (points of intersection) of the spirals, in particular helices. The material bonding engagement may be selected from the group consisting of gluing, welding such as laser welding and/or electron beam welding, melting and a combination of at least two of said material bonding engagements. The textile technique may be selected from the group consisting of weaving, knitting, braiding and a combination of at least two of said textile techniques.

In a further embodiment, the endoluminal device further comprises at least one composite yarn, i.e. one composite yarn or a plurality of composite yarns. Preferably, the at least one composite yarn comprises at least one polymer yarn, i.e. one polymer yarn or a plurality of polymer yarns, and at least one alloy wire, i.e. one alloy wire or a plurality of alloy wires. Further, the at least one composite yarn is preferably at least one covered yarn, in particular at least one wrapped yarn. Principally, the at least one alloy wire may be surrounded, in particular wrapped, preferably spirally wrapped, more preferably helically wrapped, by the at least one polymer yarn. Preferably, the at least one polymer yarn is surrounded, in particular wrapped, preferably spirally wrapped, more preferably helically wrapped, by the at least one alloy wire. Further, the at least one polymer yarn of the at least one composite yarn may comprise or consist of a different polymer as the polymer yarns described in the preceding embodiments and/or the at least one alloy wire of the at least one composite yarn may comprise or consist of a different alloy as the at least one alloy wire described in the preceding embodiments. Preferably, the at least one polymer yarn of the at least one composite yarn may comprise or consist of the same polymer as the polymer yarns described in the preceding embodiments and/or the at least one alloy wire of the at least one composite yarn may comprise or consist of the same alloy as the at least one alloy wire described in the preceding embodiments. Regarding suitable polymers for the at least one polymer yarn of the at least one composite yarn and/or alloys for the at least one alloy wire of the at least one composite yarn, reference is made in its entirety to the previous description.

Further, the polymer yarns and/or the at least one alloy wire, may be covered, in particular (only) partially covered or completely covered, by a coating. The coating may be a non-textile or textile coating. Preferably, the coating is embodied as a non-textile coating.

The coating may be advantageously adapted to increase the radial stability of the endoluminal device.

Preferably, the coating comprises or consists of a polymer, in particular a polymer which is adapted to facilitate a mutual connection of the polymer yarns and/or the at least one alloy wire, in particular by material bonding engagement such as gluing, welding or melting.

Preferably, the polymer of the coating is selected from the group consisting of polylactide, polyglycolide, poly(3-hydroxybutyrate), poly(4-hydroxybutyrate), polycaprolactone, poly(trimethylene carbonate) and a blend of at least two of said polymers.

The polylactide is preferably selected from the group consisting of poly(L-lactide), poly(D,L-lactide), poly(D-lactide) and a blend of at least two of said polymers. More preferably, the polylactide is poly(L-lactide).

Further, the polymer may be a copolymer. Preferably, the copolymer comprises or consists of repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units.

More preferably, the copolymer is selected from the group consisting of poly(L-lactide-co-glycolide), poly(D,L-lactide-co-glycolide), poly(D-lactide-co-glycolide), poly(L-lactide-co-caprolactone), poly(D,L-lactide-co-caprolactone), poly(D-lactide-co-caprolactone), poly(3-hydroxybutyrate-co-3-hydroxyvalerate), poly(3-hydroxybutyrate-co-4-hydroxybutyrate), poly(3-hydroxybutyrate-co-3-hydroxyoctanoate) and a blend of at least two of said copolymers.

It goes without saying that the polymer of the coating may be further any blend of at least two of the above-mentioned polymers and copolymers, respectively.

The coating may further comprise a degradation-retarding agent such as rubidium or compounds thereof. Thus, if the at least one alloy wire comprises or consists of a biodegradable alloy, degradation of the at least one wire can be adjusted in a timely manner.

Further, the coating may comprise at least one agent, in particular at least one anti-proliferative agent, and optionally an excipient as detailed in the following.

The endoluminal device may comprise at least one agent, i.e. one agent or a plurality of agents, and optionally at least one excipient, i.e. one excipient or a plurality of excipients. In particular, the endoluminal device may comprise a coating comprising at least one agent and optionally at least one excipient. For example, the polymer yarns and/or the at least one alloy wire may comprise at least one agent and optionally at least one excipient or a respective coating.

The at least one agent is preferably selected from the group consisting of anti-proliferative agent, antimicrobial, in particular antibiotic agent, wound healing-promoting agent, disinfecting agent, anti-inflammatory agent, growth factor, cell-differentiating factor, cell-adhesive factor, cell-recruiting factor, cell receptor, cell-binding factor, cytokine, peptide, structural protein, extracellular protein such as collagen, serum protein such as albumin, polysaccharide such as hyaluronic acid, oligonucleotide, polynucleotide, DNA, RNA, radio-opaque agent, a salt of at least two of said agents, a stereoisomer, more particular a diastereomer, of at least two of said agents and a mixture of at least two of said agents.

The at least one agent is preferably an anti-proliferative agent or a mixture of anti-proliferative agents.

The anti-proliferative agent is in particular selected from the group consisting of limus derivatives, sirolimus, everolimus, biolimus A9, tacrolimus, zotarolimus, paclitaxel, docetaxel, methotrexate, azathioprine, vincristine, vinblastine, fluorouracil, doxorubicin hydrochloride, mitomycin and a mixture of at least two of said anti-proliferative agents.

The at least one excipient may be selected from the group consisting of probucol, polyvinyl pyrrolidone, glycerine, polyhydroxyethyl, methacrylates, polyethylene glycole, polypropylene glycole, butylated hydroxytoluene (BHT), resveratol, polyvinyl alcohol, polydioxanone, polycaprolactone, polygluconate, poly(lactic acid)polyethylene oxide copolymer, modified cellulose, polyhydroxybutyrate, polyamino acids, polyphosphate esters, polyvalerolactones, poly-e-decalactones, polylactonic acid, polyglycolic acid polylactides, polyglycolides, copolymers of the polylactides and polyglycolides, poly-e caprolactone, polyhydroxybutyric acid, polyhydroxybutyrates, polyhydroxyvalerates, polyhydroxybutyrate-co-valerates, poly(1,4-dioxane-2,3-dione), poly(1,3-dioxane-2-one), poly-para-dioxanones, polyanhydrides, polymaleic acid anhydrides, polyhydroxy methacrylates, fibrin, polycyanoacrylates, polycaprolactone dimethylacrylates, poly-b-maleic acid polycaprolactone butyl acrylates, multiblock polymers from oligocaprolactonediols and oligodioxanonediols, polyether ester multiblock polymers from PEG and polybutylene terephthalate, polypivotolactones, polyglycolic acid trimethyl carbonates, polycaprolactone, glycolides, poly(g-ethyl glutamate), poly (DTH-iminocarbonate), poly(DTE-co-DT-carbonate), poly (bisphenol A-iminocarbonate), polyorthoesters, polyglycolic acid trimethyl carbonates, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, waxes, oils, polyunsaturated fatty acids, eicosapentaenoic acid, timnodonic acid, docosahexaenoic acid, arachidonic acid, linoleic acid, alpha-linolenic acid, gamma-linolenic acid, carrageenans, fibrinogen, agar-agar, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and its derivatives, heparan sulfates and its derivates, heparins, chondroitin sulfate, dextran, beta-cyclodextrins, copolymers with PEG and polypropylene glycol, gum arabic, guar, gelatin, collagen, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, polyisobutylenes, fluorosilicones, carboxymethyl chitosans, polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, EPDM gums, silicones such as polysiloxanes, polydimethylsiloxanes, polyvinyl halogens, cellulose ethers, cellulose triacetates, shellac, poly-para-xylylenes and a mixture of at least two of said excipients.

Further, at least one end, in particular ends, preferably a distal end and a proximal end, of the endoluminal device may be formed stiffened, in particular by means of a solvent treatment. For a suitable solvent treatment, solvents such as . . . and mixtures of at least two of said solvents can be used. Thus, it can be advantageously avoided that ends of the endoluminal device, in particular yarn ends thereof, fan out.

Further, the endoluminal device may be formed as a textile, in particular woven, knitted or braided, device. More preferably, the endoluminal device is embodied as a braided device.

Further, the endoluminal device may be a tubular device, in particular a tubular and textile, in particular woven, knitted or braided, device. More preferably, the endoluminal device is embodied as a tubular braided device.

Further, the endoluminal device may be a bifurcated endoluminal device.

Further, the endoluminal device may be a thermoset (heat fixed or thermo-fixed) device.

The term "thermoset device" as used according to the present invention refers to an endoluminal device which has been manufactured onto a mandrel, in particular by means of a textile technique such as weaving, knitting or braiding, and which together with the mandrel has been subsequently heated, in particular applying a temperature from 35° C. to 150° C., during a defined time, in particular during a time period of 1 minute to 1 day, in order to give the endoluminal device dimensional and shape stability.

Further, the endoluminal device may be adapted to effect a blood wall coverage, in particular a venous wall coverage or an arterial wall coverage, preferably an arterial wall coverage, in the range of 5% to 60%, in particular 10% to 50%, preferably 12% to 40%.

Further, the endoluminal device may exhibit a diameter from 1.0 mm to 10 mm, in particular 1.5 mm to 8.0 mm, preferably 2.0 mm to 6.0 mm.

Further, the endoluminal device may be a ready-for-use endoluminal device. For example, the length of the endoluminal device can be tailored by means of laser cutting.

In a further embodiment, the endoluminal device is an endovascular, in particular endovenous or endoarterial, more preferably an endoarterial, device.

More preferably, the device according to the present invention is a stent, in particular an endovascular stent, in particular an endovenous or endoarterial stent, more preferably an endoarterial stent. The stent may in particular be a self-expandable stent or a balloon-expandable stent.

It goes without saying that the endoluminal device according to the fourth aspect of the invention may be the result of any combination of the preceding disclosed embodiments.

According to a fifth aspect, the invention relates to a further method for manufacturing an endoluminal device, in particular an endoluminal device according to the fourth aspect of the invention.

The method comprises the step of
depositing a plurality of polymer yarns and at least one alloy wire onto a mandrel, wherein the polymer yarns comprise or consist of a polymer, in particular biodegradable polymer, selected from the group consisting of polylactide, polyglycolide, poly(3-hydroxybutyrate), poly(4-hydroxybutyrate), polycaprolactone, poly(trimethylene carbonate), copolymer comprising or consisting of monomer units selected from the group consisting of lactide units, glycolide units, 6-hydroxyhexanoic acid units, 3-hydroxybutyrate units, 4-hydroxybutyrate units, trimethylene carbonate units and a combination of at least two of said monomer units, and a blend of at least two of said polymers, and the at least one alloy wire comprises or consists of an alloy, in particular a biocompatible alloy, selected from the group consisting of magnesium alloy, zinc alloy, iron alloy, alloyed stainless steel, cobalt-chromium alloy and a combination of at least two of said alloys.

Preferably, the polymer yarns and/or the at least one alloy wire, in particular the polymer yarns and the at least one alloy wire, are deposited onto the mandrel by means of a textile technique, in particular by means of weaving, knitting or braiding, preferably by braiding.

Further, it is preferred that the polymer yarns and the at least one alloy wire are deposited onto the mandrel in spirals, in particular helices, along a longitudinal direction of the mandrel.

More preferably, the polymer yarns and/or the at least one alloy wire, in particular the polymer yarns and the at least one alloy wire, are deposited onto the mandrel in unidirectional spirals, in particular unidirectional helices, along a longitudinal direction of the mandrel.

Especially preferably, the polymer yarns and/or the at least one alloy wire, in particular the polymer yarns and the at least one alloy wire, are deposited onto the mandrel in oppositely directed spirals, in particular oppositely directed helices, along a longitudinal direction of the mandrel.

The polymer yarns and/or the at least one alloy wire, in particular the polymer yarns and the at least one alloy wire, may be connected to each other, preferably at crossing points (points of intersection) of the spirals, in particular helices, as mentioned in the preceding paragraphs. For example, the polymer yarns and/or the at least one alloy wire may be connected to each other by means of a textile technique such as weaving, knitting or braiding. Preferably, the polymer yarns and/or the at least one alloy wire are connected to each other by means of braiding. Alternatively, the polymer yarns and/or the at least one alloy wire may be connected to each other by material bonding engagement, such as by gluing, welding or melting.

The method may further comprise the step of
arranging enlacements (loops), in particular equidistant to each other, in a circumferential direction of the mandrel.

The enlacements (loops) may be connected to the polymer yarns and/or the at least one alloy wire, in particular to the polymer yarns and the at least one alloy wire, by means of a textile technique such as weaving, knitting or braiding or by means of a material bonding engagement such as gluing, welding or melting.

Preferably, each enlacement (loop) is embodied as composite yarn, preferably as composite yarn comprising at least one polymer yarn and at least one alloy wire. Preferably, the at least one polymer yarn comprises or consists of the same polymer as the at least one polymer yarn of the at least one composite yarn as described under the first invention aspect. Further, preferably the at least one alloy wire comprises or consists of the same alloy as the at least one alloy wire of the at least one composite yarn as described under the first invention aspect.

The method may further comprise the step of
thermosetting the endoluminal device.

Preferably, the step of thermosetting is performed at a temperature from 35° C. to 150° C. Further, the step of thermosetting may be performed during a time period of 1 minute to 1 day.

The method may further comprise the step of
subjecting the endoluminal device, in particular at least one end, in particular ends (e.g. a distal end and a proximal end), thereof to a solvent treatment.

Thus, fanning out of ends, in particular yarn ends, can be advantageously circumvented. Preferably, an organic solvent such as chloroform, dichloromethane, trichloromethane, acetone, tetrahydrofuran, ethanol or a mixture of at least two of said solvents is used for the solvent treatment.

The method may further comprise the step of
equipping the endoluminal device with at least one agent, preferably at least one anti-proliferative agent, and optionally at least one excipient.

The method may further comprise the step of
tailoring, in particular cutting, the endoluminal device.

With respect to further features and advantages of the method, reference is made in its entirety to the description of the endoluminal device according to the fourth invention aspect. The features and advantages described in terms of the endoluminal device according to the fourth invention aspect, in particular in terms of the polymer yarns and/or the at least one alloy wire and/or the at least one composite yarn and/or the enlacements, do apply accordingly with respect to the method for manufacturing an endoluminal device according to the fifth invention aspect.

According to a sixth aspect, the invention relates to a surgical system or kit, preferably for the treatment of stenosis and/or for preventing restenosis disorders.

The system and kit, respectively, comprises an endoluminal device according to the fourth aspect of the invention.

Additionally, the system and kit, respectively, comprises a delivery instrument, in particular a delivery catheter, preferably a balloon catheter.

The delivery instrument is preferably adapted to deliver the endoluminal device within a body lumen of a body vessel, in particular of a venous or arterial, preferably arterial, blood vessel.

Further, the endoluminal device is preferably attached to the delivery device, in particular crimped onto the delivery device.

Preferably, the endoluminal device is a stent.

With respect to further features and advantages of the system and kit, respectively, in particular with respect to the endoluminal device, reference is made to the embodiments described under the fourth aspect of the invention. It goes without saying that the features and advantages described in terms of the endoluminal device during the fourth aspect of the invention do apply accordingly with respect to the system and kit, respectively according to the sixth aspect of the invention.

According to a seventh aspect, the invention relates to a method for treating stenosis and/or preventing restenosis.

The method comprises the step of
implanting an endoluminal device as described in the previous description, in particular an endoluminal device according to the first or fourth aspect, in a bodily lumen, in particular vascular lumen, preferably a venous or arterial lumen, more preferably an arterial lumen.

Preferably, the lumen is a lumen of a vascular vessel, preferably a venous or arterial vessel, more preferably an arterial vessel, which suffers from stenosis or restenosis or is prone to stenosis or restenosis.

Implantation of the endoluminal device may be advantageously accomplished by a catheter, in particular balloon catheter. For that purpose, the endoluminal device is preferably adhered to, in particular crimped onto, the catheter, in particular balloon catheter.

As regards further features and advantages of the method, in particular in terms of the endoluminal device, reference is made in its entirety to the previous description. The features and advantages described therein, in particular with respect to an endoluminal device according to the first and/or fourth aspect of the invention, do apply accordingly with respect to the method for treating stenosis and/or preventing restenosis disorders according to the seventh aspect of the invention.

In the following, the present invention will be illustrated in more detail by the disclosure of preferred embodiments presented in drawings, the accompanying drawing description and in examples. In the embodiments, individual features of the invention may be realized exclusively or in combination with other features. Any described embodiment is given for the sole purpose of illustration and better understanding of the invention, and is in no way to be interpreted as a limitation.

BRIEF DESCRIPTION OF THE DRAWING FIGURES

In the FIGS. 1 to 11, different embodiments of an endoluminal device according to the present invention are schematically displayed which will be described in more detail in the following.

Figure 2:
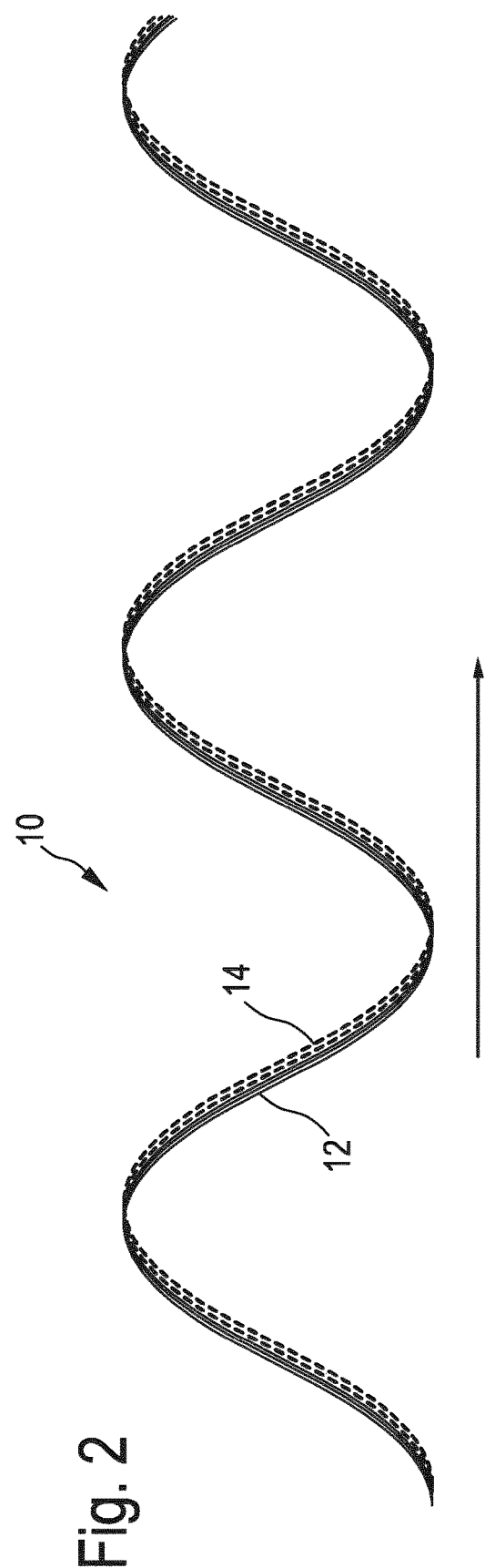

FIG. 1 schematically displays an embodiment of an endoluminal device according to one embodiment;

FIG. 2 schematically displays a further embodiment of an endoluminal device;

FIG. 3 schematically displays a further embodiment of an endoluminal device;

FIG. 4 schematically displays a further embodiment of an endoluminal device;

FIG. 5 schematically displays a further embodiment of an endoluminal device;

FIG. 6 schematically displays a further embodiment of an endoluminal device;

FIG. 7 schematically displays a further embodiment of an endoluminal device;

FIG. 8 schematically displays a further embodiment of an endoluminal device;

FIG. 9 schematically displays a further embodiment of an endoluminal device;

FIG. 10 schematically displays a further embodiment of an endoluminal device; and FIG. 11 schematically displays a further embodiment of an endoluminal device.

DETAILED DESCRIPTION

FIG. 1 schematically displays an embodiment of an endoluminal device 10 according to the present invention.

The endoluminal device 10 comprises a plurality of polymer yarns 12 and one composite yarn 14. The composite yarn 14 comprises at least one polymer yarn and at least one alloy wire. Preferably, the composite yarn 14 is a wrapped yarn. Preferably, the at least one polymer yarn is wrapped, in particular helically wrapped, by the at least one alloy wire.

The polymer yarns 12 and the composite yarn 14 extend in unidirectional helices along a longitudinal direction of the endoluminal device 10. The longitudinal direction of the endoluminal device 10 is shown as a solid arrow.

The polymer yarns 12 and the composite yarn 14 and/or the helices may be connected to each other, in particular by means of a textile technique such as weaving, knitting or braiding and/or by means of a material bonding engagement such as gluing, welding or melting.

The polymer yarns and the at least one polymer yarn of the composite yarn 14 may comprise or consist of poly(L-lactide).

The at least one alloy wire of the composite yarn may comprise or consist of a magnesium alloy.

Preferably, the endoluminal device 10 is in a thermoset condition.

Further it is preferred that the endoluminal device 10 is embodied as a stent, preferably as an endoarterial stent.

FIG. 2 schematically displays a further embodiment of an endoluminal device 10 according to the present invention.

The endoluminal device 10 comprises a plurality of polymer yarns 12 and a plurality of composite yarns 14. Each composite yarn 14 comprises at least one polymer yarn and at least one alloy wire. Preferably, each composite yarn 14 is a wrapped yarn. Preferably, the at least one polymer yarn is wrapped, in particular helically wrapped, by the at least one alloy wire.

The polymer yarns 12 and the composite yarns 14 extend in unidirectional helices along a longitudinal direction of the endoluminal device 10. The longitudinal direction of the endoluminal device 10 is shown as a solid arrow.

The polymer yarns 12 and the at least one polymer yarn of the composite yarns 14 may comprise or consist of poly(L-lactide).

The at least one alloy wire of the composite yarns 14 may comprise or consist of a magnesium alloy.

The polymer yarns 12 and the composite yarns 14 and/or the helices may be connected to each other, in particular by means of a textile technique such as weaving, knitting or braiding and/or by means of a material bonding engagement such as gluing, welding or melting.

Preferably, the endoluminal device 10 is in a thermoset condition.

Further it is preferred that the endoluminal device 10 is embodied as a stent, preferably as an endoarterial stent.

FIG. 3 schematically displays a further embodiment of an endoluminal device 10 according to the present invention.

The endoluminal device 10 comprises a plurality of polymer yarns 12 and one composite yarn 14. The composite yarn 14 comprises at least one polymer yarn and at least one alloy wire. Preferably, the composite yarn 14 is a wrapped yarn. Preferably, the at least one polymer yarn is wrapped, in particular helically wrapped, by the at least one alloy wire.

The polymer yarns 12 and the composite yarn 14 extend in oppositely directed helices along a longitudinal direction of the endoluminal device 10. The longitudinal direction of the endoluminal device 10 is shown as a solid arrow.

The polymer yarns 12 and the composite yarn 14 and/or the helices may be connected to each other, in particular by means of a textile technique such as weaving, knitting or braiding and/or by means of material bonding engagement such as gluing, welding or melting.

More preferably, at crossing points 15, the oppositely directed helices are connected to each other, in particular by means of a material bonding engagement such as gluing, welding or melting, or by means of a textile technique such as weaving, knitting or braiding. Thus, the radial stiffness of the device 10 can be additionally increased.

The polymer yarns 12 and the at least one polymer yarn of the composite yarn 14 may comprise or consist of poly(L-lactide).

The at least one alloy wire of the composite yarn 14 may comprise or consist of a magnesium alloy.

Preferably, the endoluminal device 10 is in a thermoset condition.

Further it is preferred that the endoluminal device 10 is embodied as a stent, preferably as an endoarterial stent.

FIG. 4 schematically displays a further embodiment of an endoluminal device 10 according to the present invention.

The endoluminal device 10 comprises a plurality of polymer yarns 12 and a plurality of composite yarns 14. Each composite yarn 14 comprises at least one polymer yarn and at least one alloy wire. Preferably, each composite yarn 14 is a wrapped yarn. Preferably, the at least one polymer yarn is wrapped, in particular helically wrapped, by the at least one alloy wire.

The polymer yarns 12 and the composite yarns 14 extend in oppositely directed helices along a longitudinal direction of the endoluminal device 10. The longitudinal direction of the endoluminal device 10 is shown as a solid arrow.

The polymer yarns 12 and the composite yarns 14 and/or the helices may be connected to each other, in particular by means of a textile technique such as weaving, knitting or braiding and/or by means of a material bonding engagement such as gluing, welding or melting.

More preferably, at crossing points 15, the oppositely directed helices are connected to each other, in particular by means of a material bonding engagement such as gluing, welding or melting, or by means of a textile technique such as weaving, knitting or braiding. Thus, the radial stiffness of the device 10 can be additionally increased.

The polymer yarns 12 and the at least one polymer yarn of the composite yarns 14 may comprise or consist of poly(L-lactide).

The at least one alloy wire of the composite yarns 14 may comprise or consist of a magnesium alloy.

Preferably, the endoluminal device 10 is in a thermoset condition.

Further it is preferred that the endoluminal device 10 is embodied as a stent, preferably as an endoarterial stent.

FIG. 5 schematically displays a further embodiment of an endoluminal device 10 according to the present invention.

Against the endoluminal device 10 as shown in FIG. 4, the endoluminal device of FIG. 5 additionally comprises enlacements (loops) 16 which are arranged in a circumferential direction of the endoluminal device 10. The circumferential direction of the endoluminal device 10 is indicated as a dashed arrow. Thus, the radial stiffness and/or the suspension of the device 10 can be significantly enhanced.

Each enlacement 16 is preferably made of a composite yarn, wherein the composite yarn preferably comprises at least one polymer yarn and at least one alloy wire. Preferably, the at least one polymer yarn may comprise or consist of the same polymer as the at least one polymer yarn of the composite yarns 14 described in FIG. 4 and/or the at least one alloy wire may comprise or consist of the same alloy as the at least one alloy wire of the composite yarns 14 described in FIG. 4.

Regarding further features and advantages of the endoluminal device 10, reference is made to the description of FIG. 4.

FIG. 6 schematically displays a further embodiment of an endoluminal device 10 according to the present invention.

The endoluminal device 10 comprises a plurality of polymer yarns 12 and composite yarns 14a; 14b. Each composite yarn 14a; 14b comprises at least one polymer yarn and at least one alloy wire. Preferably, each composite yarn 14a; 14b is a wrapped yarn. Preferably, the at least one polymer yarn is wrapped, in particular helically wrapped, by the at least one alloy wire.

The composite yarns 14a; 14b are differently embodied in terms of diameter of the at least one alloy wire. For example, the endoluminal device 10 may have a composite yarn 14a comprising at least one alloy wire having a diameter of 30 μm and a composite yarn 14b comprising at least one alloy wire having a diameter of 50 μm.

The polymer yarns 12 and the composite yarns 14a; 14b extend in oppositely directed helices along a longitudinal direction of the endoluminal device 10. The longitudinal direction of the endoluminal device 10 is shown as a solid arrow.

The polymer yarns 12 and the composite yarn 14a; 14b and/or the helices may be connected to each other, in particular by means of a textile technique such as weaving, knitting or braiding and/or by means of a material bonding engagement such as gluing, welding or melting.

More preferably, at crossing points 15, the oppositely directed helices are connected to each other, in particular by means of a material bonding engagement such as gluing, welding or melting, or by means of a textile technique such as weaving, knitting or braiding. Thus, the radial stiffness of the device 10 can be additionally increased.

The polymer yarns 12 and the at least one polymer yarn of the composite yarns 14a; 14b may comprise or consist of poly(L-lactide).

The at least one alloy wire of the composite yarns 14a; 14b may comprise or consist of a magnesium alloy.

Preferably, the endoluminal device 10 is in a thermoset condition.

Further it is preferred that the endoluminal device 10 is embodied as a stent, preferably as an endoarterial stent.

FIG. 7 schematically displays a further embodiment of an endoluminal device 10 according to the present invention.

The endoluminal device 10 comprises a plurality of polymer yarns 12 and a plurality of composite yarns 14, wherein each composite yarn is embodied as an enlacement (loop) 16 which is arranged in a circumferential direction of the endoluminal device 10. The circumferential direction of the device 10 is indicated as a dashed arrow. By means of the enlacements, the radial stiffness and/or suspension of the endoluminal device 10 can be significantly increased.

Each composite yarn 14 comprises at least one polymer yarn and at least one alloy wire. Preferably, each composite yarn 14 is a wrapped yarn. Preferably, the at least one polymer yarn is wrapped, in particular helically wrapped, by the at least one alloy wire.

The polymer yarns 12 extend in oppositely directed helices along a longitudinal direction of the endoluminal device 10. The longitudinal direction of the endoluminal device 10 is shown as a solid arrow.

The polymer yarns 12 and/or the helices may be connected to each other, in particular by means of a textile technique such as weaving, knitting or braiding and/or by means of a material bonding engagement such as gluing, welding or melting.

The composite yarns 14 and enlacements, respectively may be connected to the polymer yarns 12 and/or helices, in particular by means of a textile technique such as weaving, knitting or braiding or by means of material bonding engagement such as gluing, welding or melting.

The polymer yarns 12 and the at least one polymer yarn of the composite yarns 14 may comprise or consist of poly(L-lactide).

The at least one alloy wire of the composite yarns 14 may comprise or consist of a magnesium alloy.

Preferably, the endoluminal device 10 is in a thermoset condition.

Further it is preferred that the endoluminal device 10 is embodied as a stent, preferably as an endoarterial stent.

FIG. 8 schematically displays a further embodiment of an endoluminal device 10 according to the present invention.

The endoluminal device 10 comprises a plurality of polymer yarns 12 and one alloy wire 14.

The polymer yarns 12 and the alloy wire 14 extend in unidirectional helices along a longitudinal direction of the endoluminal device 10. The longitudinal direction of the endoluminal device 10 is shown as a solid arrow.

The polymer yarns 12 and the alloy wire 14 and/or the helices may be connected to each other, in particular by means of a textile technique such as weaving, knitting or braiding and/or by means of a material bonding engagement such as gluing, welding or melting.

The polymer yarns may comprise or consist of poly(L-lactide), while the alloy wire preferably comprises or consists of a magnesium alloy.

Preferably, the endoluminal device 10 is in a thermoset condition.

Further it is preferred that the endoluminal device 10 is embodied as a stent, preferably as an endoarterial stent.

FIG. 9 schematically displays a further embodiment of an endoluminal device 10 according to the present invention.

The endoluminal device 10 comprises a plurality of polymer yarns 12 and a plurality of alloy wires 14.

The polymer yarns 12 and the alloy wires 14 extend in unidirectional helices along a longitudinal direction of the endoluminal device 10. The longitudinal direction of the endoluminal device 10 is shown as a solid arrow.

The polymer yarns 12 and the alloy wires 14 and/or the helices may be connected to each other, in particular by means of a textile technique such as weaving, knitting or braiding and/or by means of a material bonding engagement such as gluing, welding or melting.

The polymer yarns may comprise or consist of poly(L-lactide), while the alloy wires preferably comprise or consist of a magnesium alloy.

Preferably, the endoluminal device 10 is in a thermo-fixed condition.

Further it is preferred that the endoluminal device 10 is a stent, preferably an endoarterial stent.

FIG. 10 schematically displays a further embodiment of an endoluminal device 10 according to the present invention.

The endoluminal device 10 comprises a plurality of polymer yarns 12 and one alloy wire 14.

The polymer yarns 12 and the alloy wire 14 extend in oppositely directed helices along a longitudinal direction of the endoluminal device 10. The longitudinal direction of the endoluminal device 10 is shown as a solid arrow.

The polymer yarns 12 and the alloy wire 14 and/or the helices may be connected to each other, in particular by means of a textile technique such as weaving, knitting or braiding and/or by means of a material bonding engagement such as gluing, welding or melting.

More preferably, at crossing points 15, the oppositely directed helices are connected to each other, in particular by means of a material bonding engagement such as gluing, welding or melting, or by means of a textile technique such as weaving, knitting or braiding. Thus, the radial stiffness of the device 10 can be additionally increased.

The polymer yarns 12 may comprise or consist of poly(L-lactide), while the alloy wire 14 preferably comprises or consists of a magnesium alloy.

Preferably, the endoluminal device 10 is in a thermoset condition.

Further it is preferred that the endoluminal device 10 is embodied as a stent, preferably as an endoarterial stent.

FIG. 11 schematically displays a further embodiment of an endoluminal device 10 according to the present invention.

The endoluminal device 10 comprises a plurality of polymer yarns 12 and a plurality of alloy wires 14.

The polymer yarns 12 and the alloy wires 14 extend in oppositely directed helices along a longitudinal direction of the endoluminal device 10. The longitudinal direction of the endoluminal device 10 is shown as an arrow.

The polymer yarns 12 and the alloy wires 14 and/or the helices may be connected to each other, in particular by means of a textile technique such as weaving, knitting or braiding and/or by means of material bonding engagement such as gluing, welding or melting.

More preferably, at crossing points 15, the oppositely directed helices a connected to each other, in particular by means of material bonding engagement such as gluing, welding or melting, or by means of textile technique such as weaving, knitting or braiding. Thus, the radial stiffness of the device 10 can be additionally increased.

The polymer yarns 12 may comprise or consist of poly(L-lactide), while the alloy wires 14 preferably comprise or consist of a magnesium alloy.

Preferably, the endoluminal device 10 is in a thermoset condition.

Further it is preferred that the endoluminal device 10 is a stent, preferably an endoarterial stent.

As regards further features and advantages of the endoluminal device 10 as depicted in the FIGS. 1 to 11, reference is made in its entirety to the general description which does apply accordingly. It goes without saying that the devices as shown in FIGS. 1 to 11, in particular the yarn(s) and/or wire(s) thereof, may also comprise or consist of alternative materials (polymers and alloys, respectively) as described in the general description.

EXAMPLES

1. Manufacture of Endoluminal Devices 1.1 Eight poly(L-lactide) yarns (100f15) were braided onto a mandrel. Additionally, wrapped yarns made of Eight poly(L-lactide) yarns (100f15) and one magnesium alloy wire were arranged as enlacements (loops) in the circumferential direction of the mandrel. The poly(L-lactide) yarns and the magnesium alloy wire had a diameter of 30 μm.

Subsequently, the braided device was thermoset onto the mandrel at 100° C. during 30 minutes. The thermoset device was removed from the mandrel and tailored to a defined length. The ends of the device were humidified with LDL7030-29/5 5% ethyl acetate solution in order to avoid a fanning out of the ends of the endoluminal device.

1.2 Six poly(L-lactide) yarns (100f15) and two wrapped yarns made of six poly(L-lactide) yarns (100f15) and a magnesium alloy wire were braided onto a mandrel. Both the poly(L-lactide) yarns and the magnesium alloy wire had a diameter of 30 μm.

Subsequently, the braided device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

1.3 six poly(L-lactide) yarns (100f15) and two wrapped yarns made of 6 poly(L-lactide) yarns (100f15) and a magnesium alloy wire were braided onto a mandrel. Both the poly(L-lactide) yarns and the magnesium alloy wire had a diameter of 30 m. Additionally, wrapped yarns made of six poly(L-lactide) yarns (100f15) and a magnesium alloy wire were arranged as enlacements (loops) in the circumferential direction of the braided device.

Subsequently, the device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

1.4 Four poly(L-lactide) yarns (100f15), two wrapped yarns made of four poly(L-lactide) yarns (100f15) and a magnesium alloy wire having a diameter of 30 μm and two wrapped yarns made of four poly(L-lactide) yarns (100f15) and a magnesium alloy wire having a diameter of 50 μm were braided onto a mandrel.

Subsequently, the braided device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

1.5 Six poly(L-lactide) yarns (100f15) and two wrapped yarns made of six poly(L-lactide) yarns (100f15) and a magnesium alloy wire were braided onto a mandrel. The poly(L-lactide) yarns had a diameter of 30 μm. The magnesium alloy wire had a diameter of 50 μm.

Subsequently, the braided device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

1.6 Seven poly(L-lactide) yarns (100f15) and one wrapped yarn made of seven poly(L-lactide) yarns (100f15) and one magnesium alloy wire were braided onto a mandrel. The poly(L-lactide) yarns had a diameter of 30 μm. The magnesium alloy wire had a diameter of 50 μm.

Subsequently, the braided device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

1.7 Six poly(L-lactide) yarns (100f15) and two magnesium alloy wires were braided onto a mandrel. The poly(L-lactide) yarns had a diameter of 30 μm, while the magnesium alloy wires had a diameter of 50 μm.

The braided device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

1.8 Four poly(L-lactide) yarns (100f15) and four magnesium alloy wires were braided onto a mandrel. The poly(L-lactide) yarns had a diameter of 30 μm while the magnesium alloy wires had a diameter of 50 μm.

The braided device was thermoset onto the mandrel at 100° C. during 30 minutes. The thermoset device was removed from the mandrel and tailored to a defined length. The ends of the device were humidified with LDL7030-29/5% ethyl acetate solution in order to avoid a fanning out of the ends of the endoluminal device.

2. Test of Compression Behaviour

Four different designs of an endoluminal device were manufactured.

The first design, in the following denoted as EKU 01, had a spiral configuration made of eight fibres of poly(L-lactide) together with one magnesium alloy wire. Both the fibres of poly(L-lactide) and the magnesium alloy wire had a diameter of 30 μm.

The second design, in the following denoted as EUF 01, had a braided configuration made of eight fibres of poly(L-lactide) only.

The third design, in the following denoted as EUF 03, had a braided configuration made of eight fibres of poly(L-lactide) with composite yarns made of eight filaments of poly(L-lactide) together with one magnesium alloy wire, wherein the composite yarns were arranged as enlacements (loops) in the circumferential direction of the endoluminal device. While the fibres of poly(L-lactide) had a diameter of 30 μm, the magnesium alloy wire had a diameter of 50 μm.

The fourth design, in the following denoted as EUF 06, had a braided configuration made of eight fibres of poly(L-lactide) and one magnesium alloy wire. While the fibres of poly(L-lactide) had a diameter of 30 μm, the magnesium alloy wire had a diameter of 50 μm.

The aim of the investigation was to study the behaviour of the above designs under compression in comparison to a drug eluting stent of the last generation of Coroflex ISAR Neo.

The designs were tested before and after drug coating. The coating was the same coating as used in Coroflex ISAR DES. The aim was to see possible changes in stability after coating.

In order to see the deformation during compression, a new test method was developed to measure the radial resistance with parallel plates according to ISO 25539-2:2012 (point 8.6.2.4, crush resistance with parallel plates). It was the determination of the load required to cause clinically relevant buckling or a deflection reduction of at least 50% of the original distance between the plates or of the expanded stent diameter.

The developed scaffolds exhibited self-memory properties. Therefore, two compression cycles were planned to analyze the self-memory properties of uncoated pieces.

The test results without coating are shown in the below table 1.

The lowest compression value was measured with the coil design EKU 01 of 0.01 N and the highest compression was measured with the radially mounted enlacements in the scaffold type EUF 03 of 0.046 N. The second compression of the designs showed the same compression forces (values in table 1 with the identification "measurement 2") and similar correlation in force versus displacement behaviours compared to the first measurements.

TABLE 1

Measurements of the maximal compression forces of the designs without coating at a 50% inner diameter reduction and the measurements of the second compression cycle are indicated with "measurement 2".

| Probe labelling | $F_{max}$ [N] |
| --- | --- |
| EUF 01 | 0.17 |
| EUF 01 "measurement 2" | 0.17 |
| EUF 03 | 0.46 |
| EUF 03 "measurement 2" | 0.47 |
| EUF 06 | 0.16 |
| EUF 06 "measurement 2" | 0.16 |
| EKU 01 | 0.02 |
| EKU 01 "measurement 2" | 0.02 |

After design coating the compression forces were measured in order to study the mechanical effect of the coating. The maximal compression forces are indicated in the below table 2.

TABLE 2

Measurements of the maximal compression forces of coating designs at a 50% inner diameter reduction in comparison to the latest generation drug eluting stent design Coroflex ISAR Neo.

| Probe labelling | $F_{max}$ [N] |
| --- | --- |
| Cx ISAR Neo 4.0 × 38 mm | 2.75 |
| EKU 01 | 0.13 |
| EUF 01 | 0.44 |
| EUF 03 | 1.02 |
| EUF 06 | — |
| EUF 06 | 0.45 |

Evaluation:

The designs had an important influence on the reaction during compression. The radial filament arrangements the scaffold design increased the reaction force about 2.7 times. Due to the coating, the compression force of design "EUF 03" increased about two times compared to the scaffold without coating.

The compression force of a drug eluting stent of the latest generation was about 2.7 N. The achieved compression force of the coated design "EUF 03" was about 1.02 N. This is a relation of less than one third of a drug eluting stent. The increase of wall thickness was about 100 μm in those locations where free fiber layers overlapped. The wall thickness in the locations where only two fiber layers overlapped was about 60 μm.

The arrangement of the 30 μm fibres of magnesium and poly(L-lactide) and the coating had an influence on the compression force of the designs.

The invention claimed is:

1. An endoluminal device comprising at least one composite yarn,
   wherein the at least one composite yarn comprises at least one polymer yarn and at least one alloy wire,
   wherein the at least one polymer yarn comprises a biodegradable polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers, and
   the at least one alloy wire comprises magnesium alloy, zinc alloy, iron alloy, cobalt-chromium alloy or combinations thereof,
   wherein the at least one composite yarn is a wrapped yarn, and wherein the at least one polymer yarn is spirally wrapped by the at least one alloy wire,
   wherein the endoluminal device additionally comprises at least one non-composite yarn consisting of polymer, wherein the at least one non-composite yarn and the at least one composite yarn are connected to each other by means of a textile technique to form a tubular device.

2. The endoluminal device according to claim 1, wherein the at least one polymer yarn comprises polylactide and/or a copolymer comprising lactide units.

3. The endoluminal device according to claim 1, wherein the at least one alloy wire comprises a magnesium alloy.

4. The endoluminal device according to claim 1, wherein the at least one non-composite yarn consists of the same polymer as the at least one polymer yarn of the at least one composite yarn.

5. The endoluminal device according to claim 1, wherein the at least one composite yarn and the at least one non-composite yarn extend in oppositely directed spirals along a longitudinal direction of the endoluminal device.

6. The endoluminal device according to claim 5, wherein the spirals are connected to each other.

7. The endoluminal device according to claim 1, wherein the at least one composite yarn and/or the at least one non-composite yarn extend in unidirectional spirals along a longitudinal direction of the endoluminal device.

8. The endoluminal device according to claim 1, wherein the at least one composite yarn comprises a plurality of composite yarns.

9. The endoluminal device according to claim 1, wherein the endoluminal device comprises a plurality of the composite yarns, wherein a number of the plurality of the composite yarns extend along a longitudinal direction of the endoluminal device and a remaining number of the plurality of the composite yarns is arranged in a circumferential direction of the endoluminal device or surrounds the endoluminal device along its circumference.

10. The endoluminal device according to claim 1, wherein the endoluminal device further comprises a coating.

11. The endoluminal device according to claim 1, wherein the endoluminal device is a stent.

12. The endoluminal device according to claim 1, wherein the textile technique is selected from the group consisting of weaving, knitting, braiding and a combination of at least two of said textile techniques.

13. The endoluminal device according to claim 1, wherein the endoluminal device comprises additional composite yarns in the form of enlacements each being arranged perpendicularly to the longitudinal axis of the endoluminal device.

14. An endoluminal device comprising of at least one composite yarn,
   wherein the at least one composite yarn comprises at least one polymer yarn and at least one alloy wire,
   wherein the at least one polymer yarn comprises a biodegradable polymer selected from the group consisting of polylactide, polyglycolide, poly(3-hydroxybutyrate), poly(4-hydroxybutyrate), polycaprolactone, poly(trimethylene carbonate), copolymer comprising repeating monomer units selected from the group consisting of lactide units, glycolide units, 6-hydroxyhexanoic acid units, 3-hydroxybutyrate units, 4-hydroxybutyrate units, trimethylencarbonate units and a combination of at least two of said monomer units, and a blend of at least two of said polymers, and
   the at least one alloy wire comprises magnesium alloy, zinc alloy, iron alloy, cobalt-chromium alloy or combinations thereof,
   wherein the at least one composite yarn is a wrapped yarn, and wherein the at least one polymer yarn is spirally wrapped by the at least one alloy wire, wherein the endoluminal device additionally comprises at least one non-composite yarn consisting of polymer, wherein the at least one non-composite yarn and the at least one composite yarn are connected to each other by means of a textile technique to form a tubular device and wherein the endoluminal device additionally comprises a non-textile coating, wherein the non-textile coating covers the at least one composite yarn and/or the at least one non-composite yarn.

15. The endoluminal device according to claim 14, wherein the non-textile coating covers the at least one alloy wire of the at least one composite yarn.

16. The endoluminal device according to claim 14, wherein the non-textile coating covers the at least one polymer yarn of the at least one composite yarn.

17. The endoluminal device according to claim 14, wherein the non-textile coating covers the at least one composite yarn only partially.

18. The endoluminal device according to claim 14, wherein the non-textile coating covers the at least one composite yarn completely.

19. The endoluminal device according to claim 14, wherein the non-textile coating comprises at least one agent.

* * * * *